US006368814B1

(12) United States Patent
Ghoshal et al.

(10) Patent No.: US 6,368,814 B1
(45) Date of Patent: Apr. 9, 2002

(54) TRICYCLIC ANTIDEPRESSANT DERIVATIVES AND IMMUNOASSAY

(75) Inventors: Mitali Ghoshal, Noblesville; Jane S. C. Tsai, Indianapolis; Stephen Vitone, Noblesville, all of IN (US)

(73) Assignee: Roche Diagnostics Corporation, Indianapolis, IN (US)

( * ) Notice: Subject to any disclaimer, the term of this patent is extended or adjusted under 35 U.S.C. 154(b) by 0 days.

(21) Appl. No.: 09/747,809

(22) Filed: Dec. 22, 2000

(51) Int. Cl.[7] ............... G01N 33/535; G01N 33/543; C07K 16/44; C07K 17/06; C07D 223/18; C07D 207/46

(52) U.S. Cl. ............... 435/7.93; 436/525; 436/529; 436/533; 436/545; 436/546; 436/815; 530/388.9; 530/389.8; 530/405; 540/591; 548/528

(58) Field of Search ............... 435/7.93; 436/525, 436/529, 533, 545, 546, 815; 530/388.9, 389.8, 405; 540/591; 548/528

(56) References Cited

U.S. PATENT DOCUMENTS

| | | | |
|---|---|---|---|
| 4,629,691 A | * | 12/1986 | Collins et al. |
| 5,256,409 A | * | 10/1993 | Blincko |
| 5,413,911 A | * | 5/1995 | Adamczyk et al. |
| 5,618,926 A | * | 4/1997 | Salamone et al. |

FOREIGN PATENT DOCUMENTS

| | | | | |
|---|---|---|---|---|
| EP | 107134 | * | 5/1984 | |
| EP | 0226730 B1 | | 7/1987 | ......... C07D/223/28 |
| WO | WO-97/08192 | * | 3/1997 | |

OTHER PUBLICATIONS

Hubbard, J.W. et al., "Radioimmunoassay for Psychotropic Drugs II: Synthesis and Properties of Haptens for Tricyclic Antidepressants" Journal of Pharmaceutical Sciences/ vol. 67, No. 11, Nov. 1978 (pp. 1571–1578).

* cited by examiner

Primary Examiner—Mary E. Ceperley
(74) Attorney, Agent, or Firm—Marilyn Amick; Roche Diagnostics Corporation

(57) ABSTRACT

The present invention is directed to novel tricyclic antidepressant drug derivatives synthesized for covalent attachment to proteins or polypeptide antigens for use in the preparation of antibodies or receptors to tricyclic antidepressant drugs and tricyclic antidepressant metabolites. The new derivatives are characterized by a saturated double bond on the amitriptyline portion of the molecule and are represented by the structure

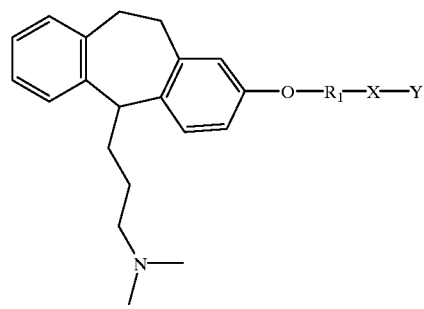

where $R_1$ is a saturated or unsaturated, substituted or unsubstituted, straight or branched chain of 0–10 carbon or heteroatoms, X is a linker group consisting of 0–2 substituted or unsubstituted aromatic rings, and Y is an activated ester or NH—Z, where Z is a poly(amino acid). The novel tricyclic antidepressant activated hapten derivatives are useful for preparing tracers and conjugates for tricyclic antidepressant immunoassays, including an enzyme immunoassay and a microparticle capture inhibition assay using an antibody produced from the novel immunogen with a conjugate derivatized either at the N-1 position of imipramine or at the C-2 position of dihydroamitriptyline.

10 Claims, 13 Drawing Sheets

4-aminomethylbenzoic acid

| CH₃OH
| SOCl₂
↓

20
methyl 4-aminomethylbenzoate hydrochloride

27

28

29

30

TRICYCLIC ANTIDEPRESSANT DERIVATIVES AND IMMUNOASSAY

BACKGROUND OF THE INVENTION

This invention relates generally to the field of measuring an analyte in a liquid medium. More specifically, it relates to an immunoassay and reagents useful for the determination of an analyte in a biological sample, and in particular, for the determination of tricyclic antidepressant drugs.

SUMMARY OF THE INVENTION

The present invention relates to a new tricyclic antidepressant (TCA) immunogen useful for the generation of polyclonal and monoclonal antibodies to TCAs. The new immunogen is characterized by a saturated double bond on the amitriptyline portion of the molecule (dihydro amitriptyline). The invention also relates to TCA activated hapten derivatives useful for preparing tracers and conjugates for TCA immunoassays using an antibody produced from the immunogen of structure I derivatized at the C-2 position with either a conjugate derivatized at the N-1 position of imipramine or a conjugate derivatized at the C-2 position of dihydro-amitriptyline. The immunoassays of the present invention include a single, qualitative or semiquantitative toxicological screening assay which would broadly recognize tricyclic antidepressants as a class.

The present invention comprises the following embodiments:

a compound having the structure

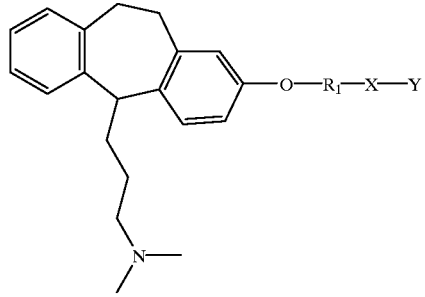

I where $R_1$ is a saturated or unsaturated, substituted or unsubstituted, straight or branched chain of 0–10 carbon or heteroatoms, X is a linker group consisting of 0–2 substituted or unsubstituted aromatic rings, and Y is an activated ester or NH—Z, where Z is a poly(amino acid);

an immunogen having the structure

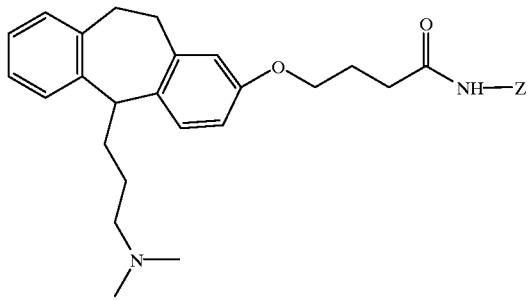

II where Z is a poly(amino acid);

an antibody produced in response to an immunogen of structure II;

an activated hapten having the structure

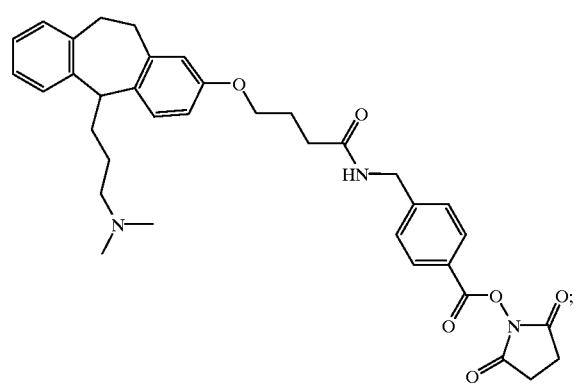

III an activated hapten having the structure

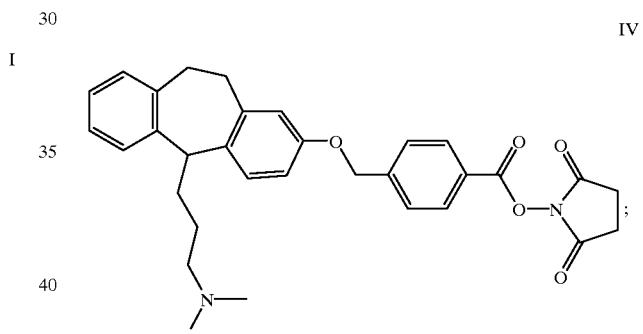

IV an activated hapten having the structure

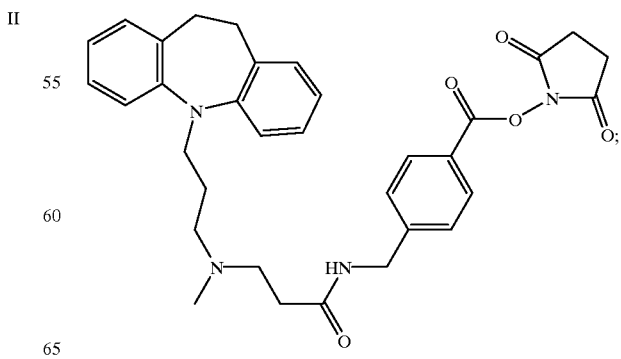

V an activated hapten having the structure

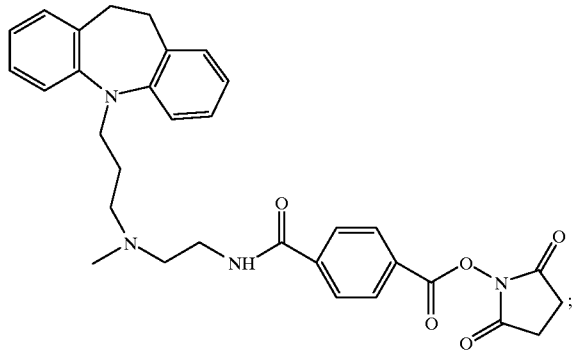

VI an immunoassay for a tricyclic antidepressant drug utilizing an antibody produced from an immunogen of structure II and a drug conjugate derived from structure III, IV, V and VI, an immunoassay for a tricyclic antidepressant drug utilizing an antibody specific for a tricyclic antidepressant and a drug conjugate derived from structure III, IV, V and VI; and an immunoassay for a tricyclic antidepressant drug utilizing an antibody produced from an immunogen of structure II and a tricyclic antidepressant drug analog.

DETAILED DESCRIPTION OF THE INVENTION

Figure 1A:
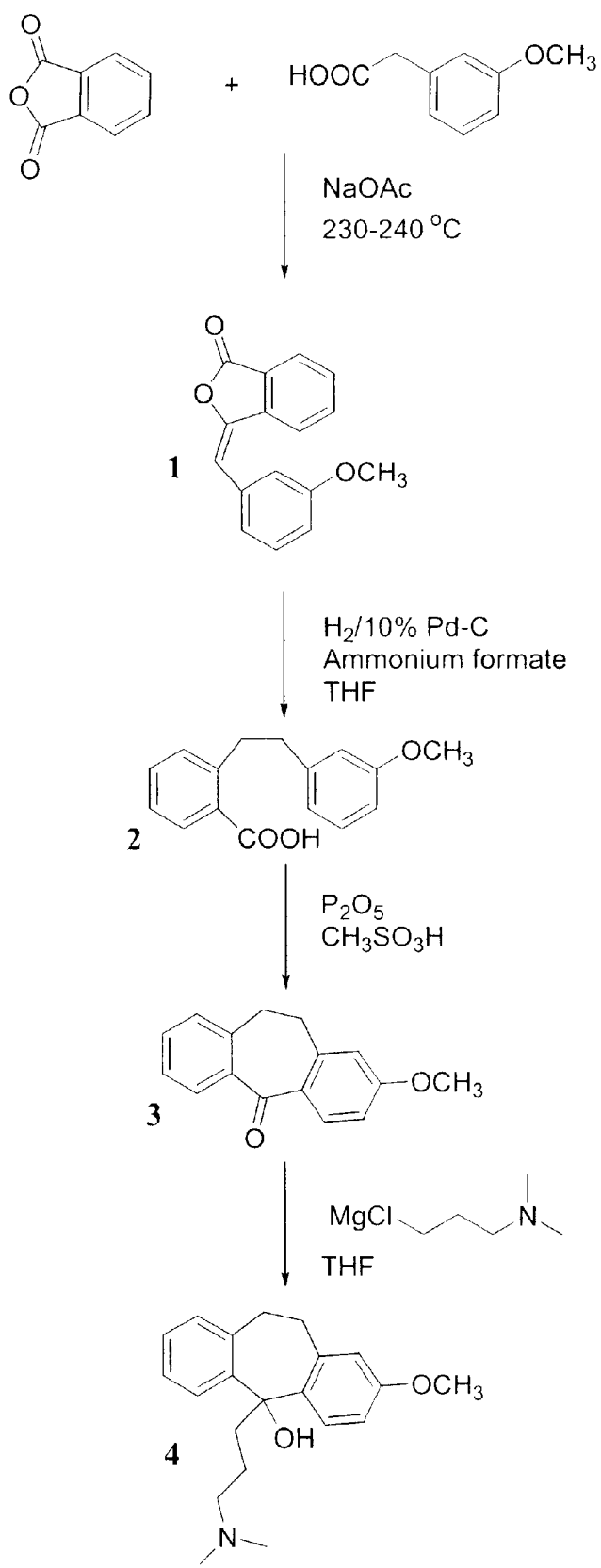
FIGS. 1(a), 1(b) and 1(c) are schematic diagrams illustrating the synthesis of two protein conjugates of the present invention, compounds 10 and 11 (structure II).
Figure 1B:
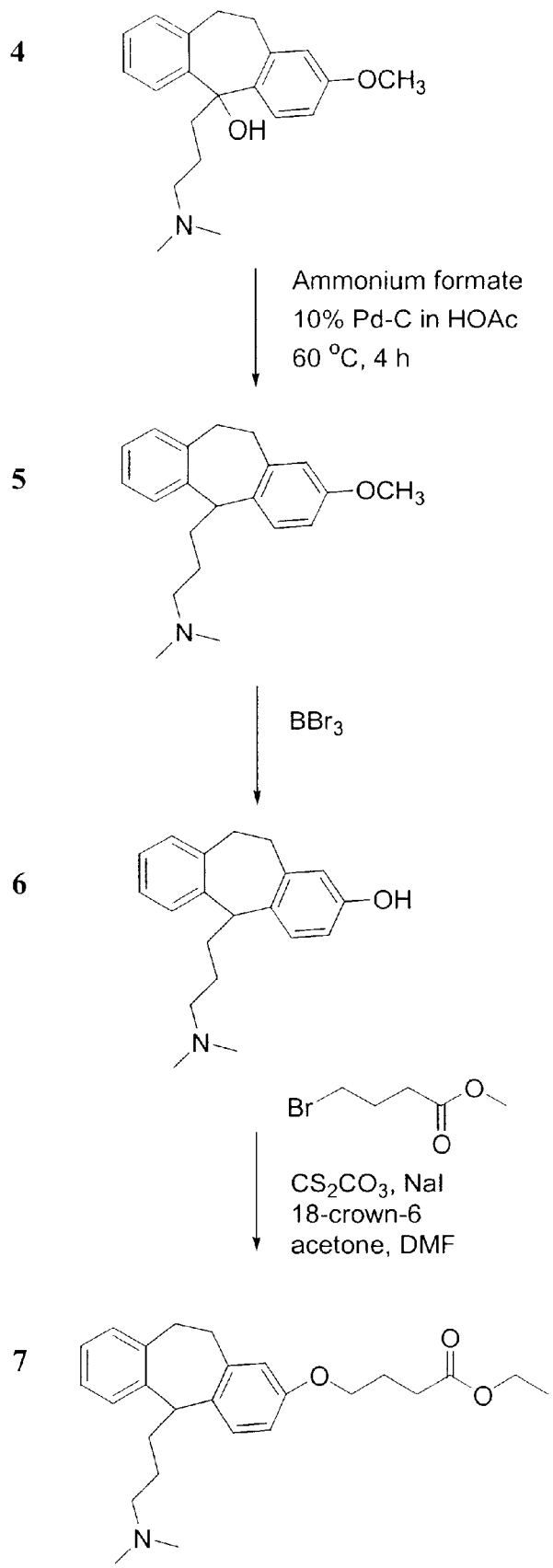
Figure 1C:
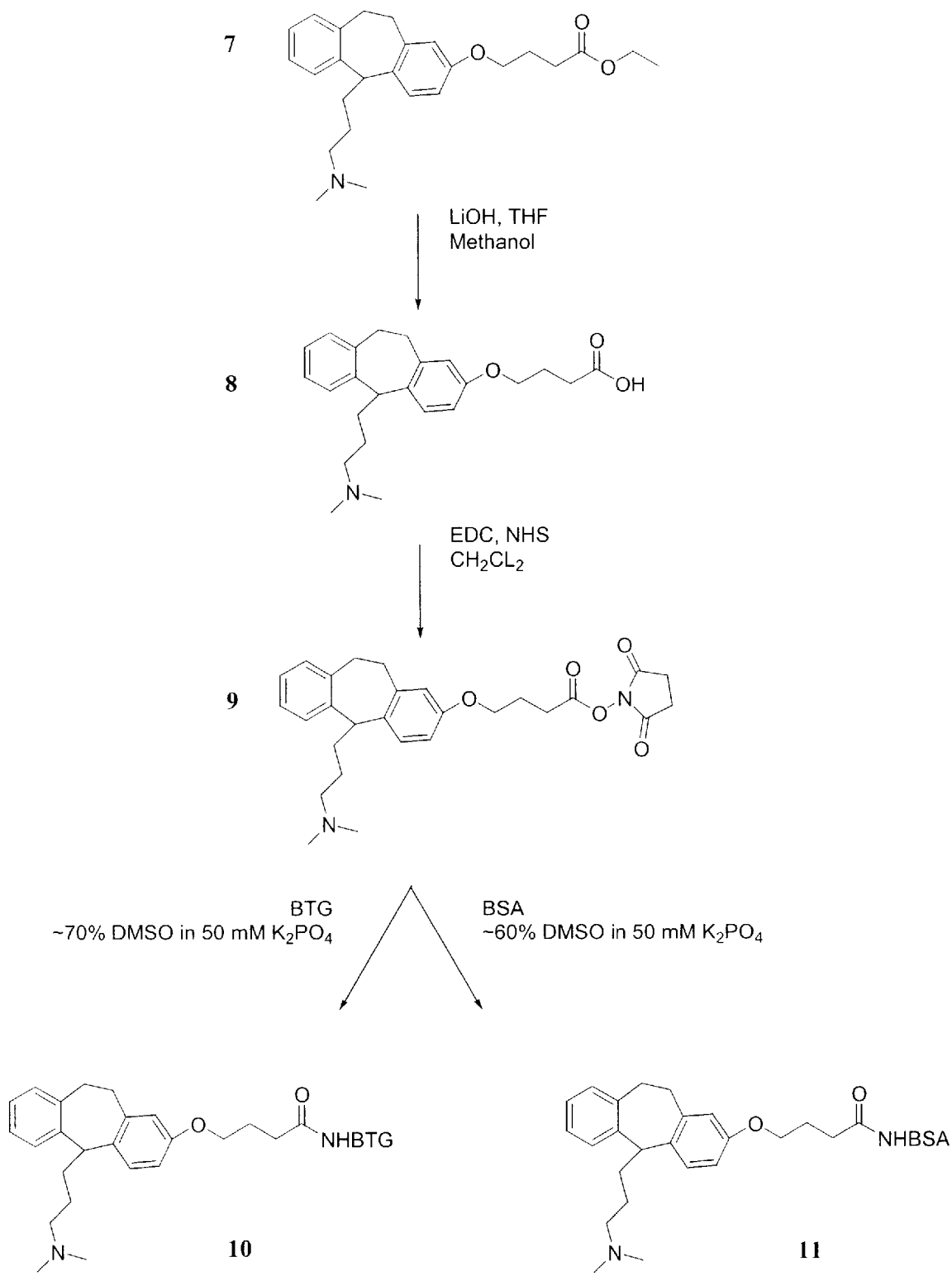
Figure 2:
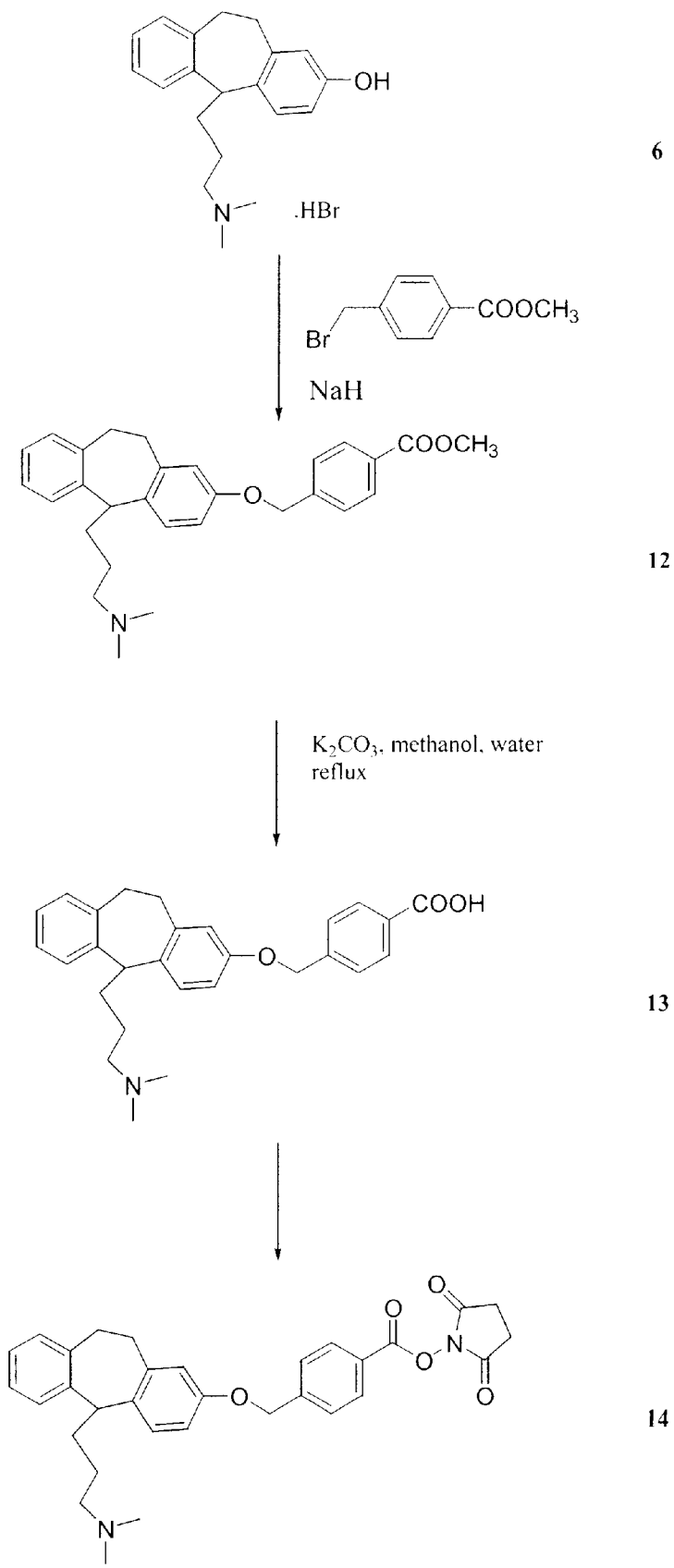
FIG. 2 is a schematic diagram illustrating the synthesis of compound 14 (structure IV).
Figure 3:
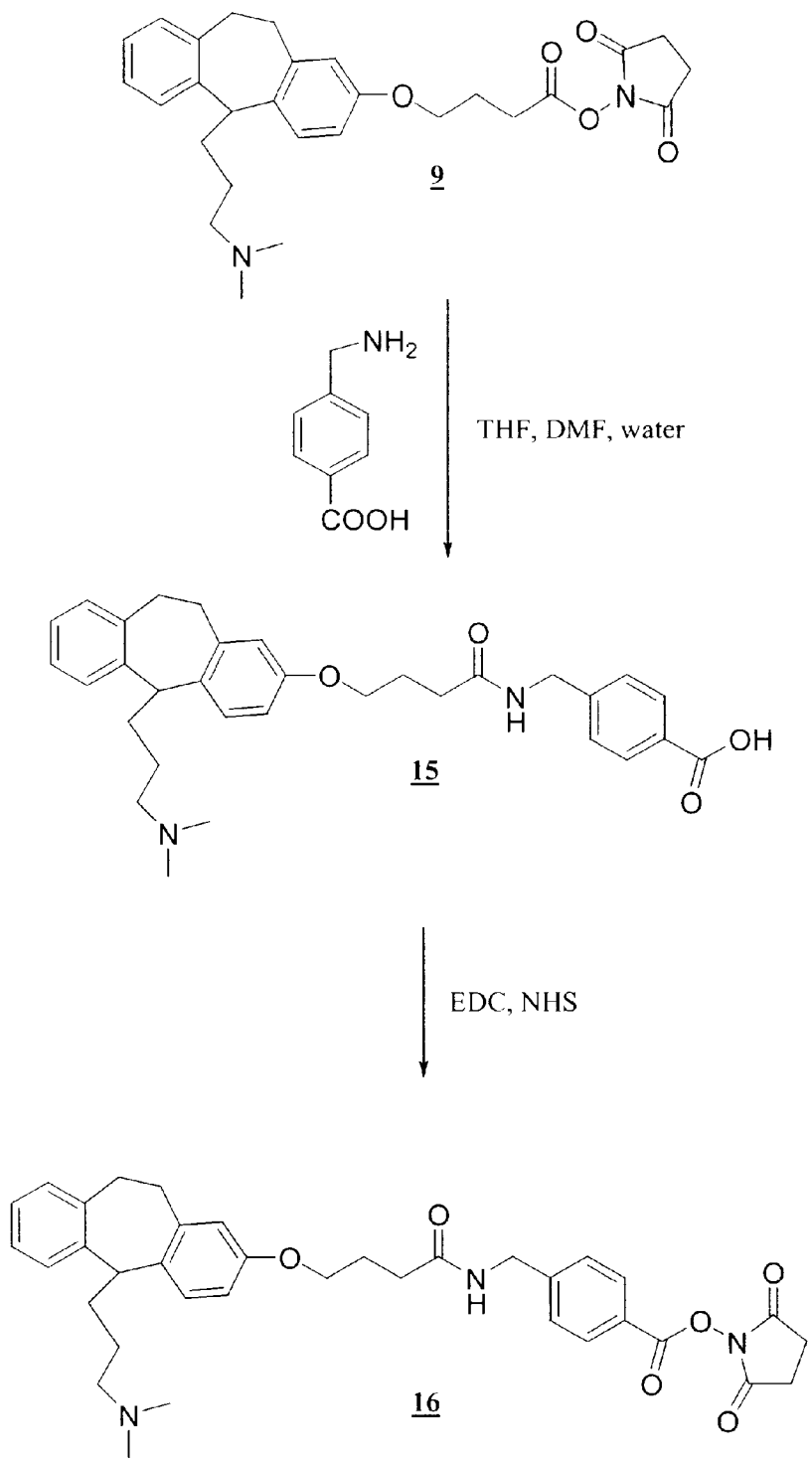
FIG. 3 is a schematic diagram illustrating the synthesis of compound 16 (structure III).
Figure 4A:
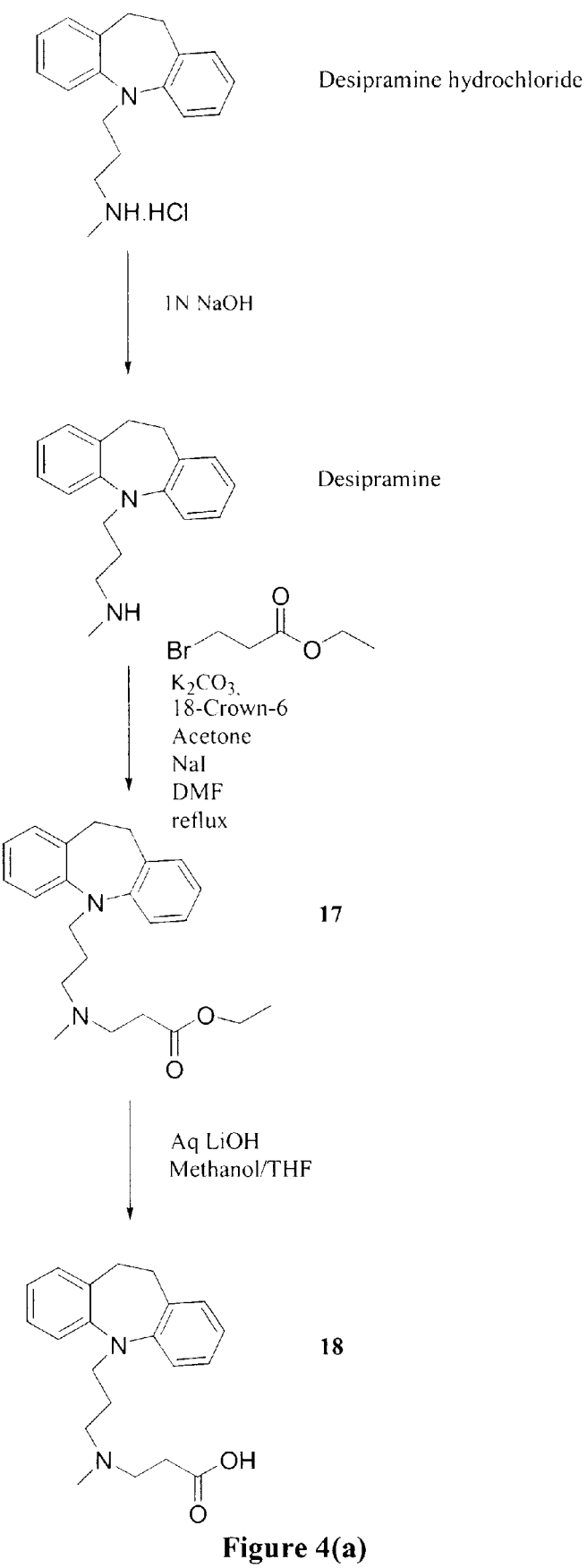
FIGS. 4(a) and 4(b) are schematic diagrams illustrating the synthesis of compound 22 (structure V).
Figure 4B:
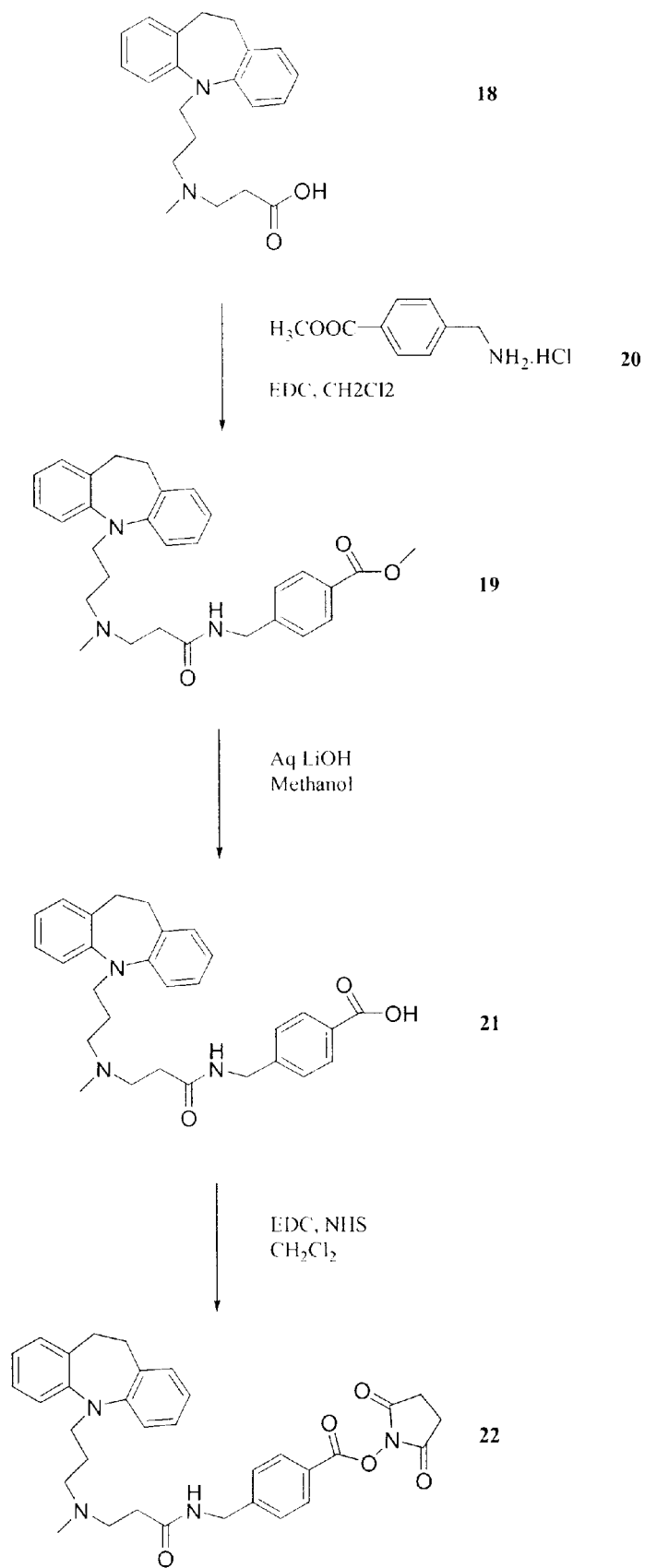
Figure 4C:
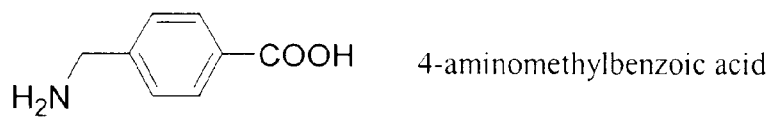
FIG. 4(c) is a schematic diagram illustrating the synthesis of methyl 4-aminomethylbenzoate hydrochloride (compound 20) used in the synthesis of compound 22.
Figure 4C:
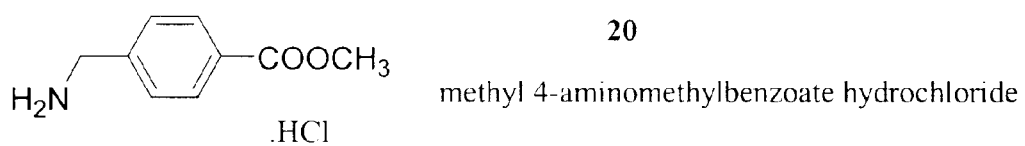
Figure 5:
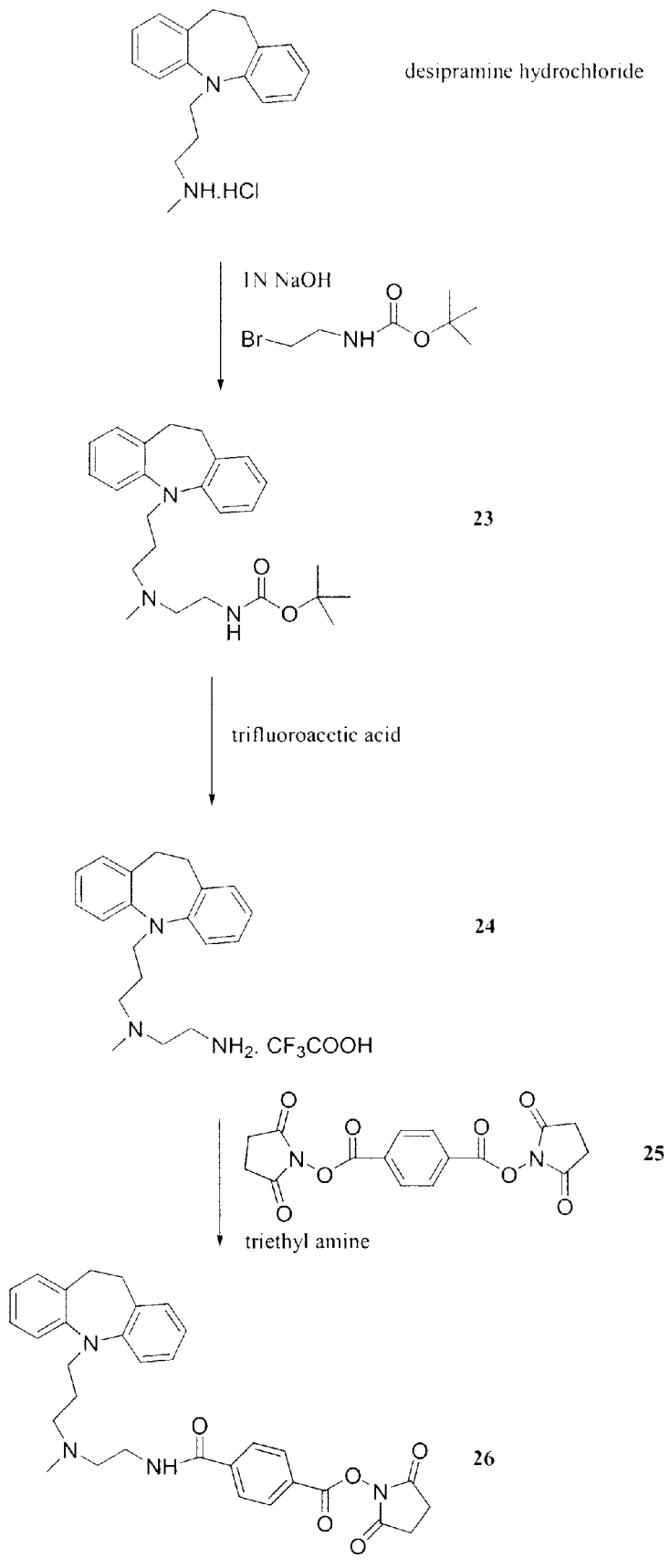
FIG. 5 is a schematic diagram illustrating the synthesis of compound 26 (structure VI).

Tricyclic antidepressant compounds which may be detected in an assay in accordance with the present invention include derivatives of dibenzazepine, dibenzocycloheptadiene and dibenzoxepine characterized by the formula

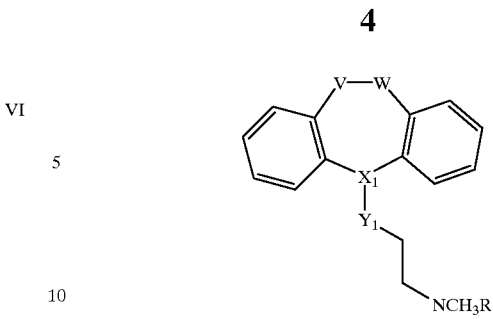

wherein V is $CH_2$ or $CH=$, W is $CH_2$, O or $=CH$, $X_1$ is N or $C=$, $Y_1$, is $CH_2$ or $=CH-$ and R is H or $CH_3$. Exemplary of such tricyclic antidepressant compounds are imipramine, desipramine, amitriptyline, nortriptyline, protriptylene, trimipramine, chlomipramine and doxepin.

In testing for small analytes such as drug molecules, immunoassays, particularly competitive binding immunoassays, have proven to be especially advantageous. In competitive binding immunoassays, an analyte in a biological sample competes with a labeled reagent, or analyte analog, or tracer, for a limited number of receptor binding sites on antibodies specific for the analyte and analyte analog. Enzymes such as β-galactosidase and peroxidase, fluorescent molecules such as fluorescein compounds, radioactive compounds such as $^{125}I$, and microparticles are common labeling substances used as tracers. The concentration of analyte in the sample determines the amount of analyte analog which will bind to the antibody. The amount of analyte analog that will bind is inversely proportional to the concentration of analyte in the sample, because the analyte and the analyte analog each bind to the antibody in proportion to their respective concentrations. The amount of free or bound analyte analog can then be determined by methods appropriate to the particular label being used.

Various protein types may be employed as the poly(amino acid) antigenic material. These types include albumins, serum proteins, e.g., globulins, ocular lens proteins, lipoproteins and so forth. Illustrative proteins include bovine serum albumin, keyhole limpet hemocyanin, egg ovalbumin, bovine gamma-globulin and so forth. Alternatively, aminopolysaccharides, such as aminodextran, or synthetic poly (amino acid)s may be prepared having a sufficient number of available amino groups, e.g., lysines.

In the method of the invention, a sample suspected of containing imipramine, desipramine, amitriptyline, nortriptyline or a structurally related drug is combined with an antibody having specificity for imipramine, desipramine, amitriptyline, or nortriptyline and a labeled analyte analog which can interact with the combination of antibody and its corresponding analyte so as to detect the presence of the analytes at selected cutoff levels either alone or in combination. This invention can be used with any type of immunoassay format, e.g., turbidometric agglutination assay, radioimmunoassay, enzyme immunoassay, fluorescent polarization immunoassay or lateral flow immunochromatography. A potential use of the present invention is with agglutinometric formats susceptible to an instrumental method for the measurement of the changes brought about by the agglutination reaction. Both manual as well as automated apparatus testing may be suitably employed for such agglutinometric analysis. Typically, automated instrumentation will operate utilizing a multiplicity of reagent containers or reservoirs from which will be pipetted the appropriate amount of each reagent for addition to the sample. For immunoassays such as the subject agglutination assay, this will usually involve at least two such containers, typically, one for an antibody reagent and the other for the microparticles bound with the corresponding ligand. Alternatively, one container may comprise ligand analog conjugate reagent and the other comprises microparticles bound with antibody. Additional containers or reservoirs may be present in some instruments containing diluent, buffers or other additives for appropriate treatment of the sample.

The clinical analyzer pipettes the onboard reagents and samples into one cuvette where the competitive agglomeration reaction occurs and measurement of the turbidity is made. For example, using the HITACHI 917 analyzer (Roche Diagnostics) and the ABUSCREEN® OnLine drugs of abuse reagent kit (Roche Diagnostics), urine sample is pipetted with sample diluent into the cuvette, followed immediately by the appropriate amount of antibody reagent and mixing. An initial spectrophotometer reading is taken. Then the appropriate quantity of microparticle reagent is transferred to the cuvette and the reaction mixed. After a brief incubation, a final turbidity measurement is made. The overall change in turbidity (absorbance) in the reaction is compared to a calibration curve and results reported in ng/ml.

Microwell-plate based ELISA (enzyme-linked immunosorbent assay) is an established technology that has been widely applied to develop enzyme immunoassays for various analytes and proteins. Competitive ELISA has been applied for developing sensitive enzyme immunoassays for small analytes such as drug molecules. The present invention can be used in competitive ELISA for the quantification of TCAs in biological fluids. In the method of the invention, a sample suspected of containing, for example, imipramine or structurally related compounds, is diluted and added into microwell plates pre-coated with any of the TCA conjugates disclosed in the present invention, followed by pre-determined amount of anti-TCA antibody. After incubation, the wells can be processed with the standard ELISA procedure (appropriate enzyme-labeled secondary antibody, substrate, wash steps in between, and the measurement of optical densities). Optical densities can be plotted versus the final concentration of imipramine or TCA structurally-related compound selected as calibrator and calculated as a molar concentration.

Fluorescence polarization immunoassay procedures provide a quantitative means for measuring the amount of tracer-antibody conjugate produced in a competitive binding immunoassay. Such fluorescence polarization techniques are based on the principle that a fluorescent labeled compound, when excited by plane polarized light, will emit fluorescence having a degree of polarization inversely related to its rate of rotation. Accordingly, when a tracer-antibody conjugate having a fluorescent label is excited with plane polarized light, the emitted light remains highly polarized because the fluorophore is constrained from rotating between the time that light is absorbed and emitted. In contrast, when an unbound tracer is excited by plane polarized light, its rotation is much faster than the corresponding tracer-antibody conjugate and the molecules are more randomly oriented. As a result, the light emitted from the unbound tracer molecules is depolarized.

Lateral flow immunochromatography has been utilized to develop a rapid, non-instrument based strip assay for qualitative immunoassays. The immunochromatographic strip assay is based on the principle of competitive immunoassay whereby drug in the urine competes with a membrane-impregnated drug conjugate for the specific antibody on colored microparticles such as gold sol or dyed latex. The appearance of a colored bar at the detection region (drug impregnation area) for the drug indicates a negative result. No band is observed if the drug is present in the urine sample at or above the cutoff concentration for the corresponding assay. The present invention is useful for the development of membrane strip devices that serve as a toxicological screening immunoassay for the TCAs.

By tricyclic antidepressant (TCA) is meant any one of a group of drugs commonly used for treatment of depression, all of which have a similar chemical structure, a triple ring with a methylaminopropane side-chain. Exemplary of this group are imipramine, desipramine, amitriptyline, nortriptyline, protriptylene, trimipramine, chlomipramine, doxepin as well as biologically active or therapeutically active derivatives and metabolites thereof.

Analyte refers to the substance, or group of substances, whose presence or amount thereof in a liquid medium is to be determined and is meant to include any drug or drug derivative, hormone, protein antigen or oligonucleotide.

Analyte analog means any substance, or group of substances, which behaves essentially the same as the analyte with respect to binding affinity of the antibody for the analyte and is meant to include any tricyclic antidepressant drug or derivative and metabolites and isomers thereof.

Antibody or receptor means a specific binding partner of the analyte and is meant to include any substance, or group of substances, which has a specific binding affinity for the analyte to the exclusion of other substances. The term includes polyclonal antibodies, monoclonal antibodies and antibody fragments.

Haptens are partial or incomplete antigens. They are protein-free substances, mostly low molecular weight substances, which are not capable of stimulating antibody formation, but which do react with antibodies. The latter are formed by coupling the hapten to a high molecular weight carrier and injecting this coupled product into humans or animals. Examples of haptens include therapeutic drugs such as digoxin and theophylline, drugs of abuse such as morphine and LSD, antibiotics such as gentamicin and vancomycin, hormones such as estrogen and progesterone, vitamins such as vitamin B12 and folic acid, thyroxin, histamine, serotonin, adrenaline and others.

An activated hapten refers to a hapten derivative that has been provided with an available site for reaction such as by the attachment of a linking group for synthesizing a derivative conjugate.

A carrier, as the term is used herein, is an immunogenic substance, commonly a protein, that can join with a hapten, thereby enabling the hapten to stimulate an immune response. Carrier substances include proteins, glycoproteins, complex polysaccharides and nucleic acids that are recognized as foreign and thereby elicit an immunologic response from the host.

The terms immunogen and immunogenic as used herein refer to substances capable of producing or generating an immune response in an organism.

The term derivative refers to a chemical compound or molecule made from a parent compound or molecule by one or more chemical reactions.

Linking groups are used to activate, i.e., provide an available site on a drug derivative for synthesizing a hapten. The use of a linking group may or may not be advantageous or needed, depending on the specific hapten and carrier pairs. The term linker refers to a chemical moiety that connects a hapten to a carrier, immunogen, label, tracer or another linker. Linkers may be straight or branched, saturated or unsaturated carbon chains. They may also include one or more heteroatoms within the chain or at termini of the chains. By heteroatoms is meant atoms other than carbon which are chosen from the group consisting of oxygen, nitrogen and sulfur.

As used herein, a detector molecule, label or tracer is an identifying tag which, when attached to a carrier substance or molecule, can be used to detect an analyte. A label may be attached to its carrier substance or antibody directly or indirectly by means of a linking or bridging moiety. Examples of labels include enzymes such as β-galactosidase and peroxidase, fluorescent compounds such as rhodamine and fluorescein isothiocyanate (FITC), luminescent compounds such as dioxetanes and luciferin, and radioactive isotopes such as $^{125}$I.

A peptide is any compound formed by the linkage of two or more amino acids by amide (peptide) bonds, usually a polymer of α-amino acids in which the α-amino group of each amino acid residue (except the $NH_2$-terminal) is linked to the α-carboxyl group of the next residue in a linear chain. The terms peptide, polypeptide and poly(amino acid) are used synonymously herein to refer to this class of compounds without restriction as to size. The largest members of this class are referred to as proteins.

Any sample that is reasonably suspected of containing the analyte, i.e., a tricyclic antidepressant drug, can be analyzed by the method of the present invention. The sample is typically an aqueous solution such as a body fluid from a host, for example, urine, whole blood, plasma, serum, saliva, semen, stool, sputum, cerebral spinal fluid, tears, mucus or the like, but preferably is plasma or serum. The sample can be pretreated if desired and can be prepared in any convenient medium that does not interfere with the assay. An aqueous medium is preferred.

Figure 6:
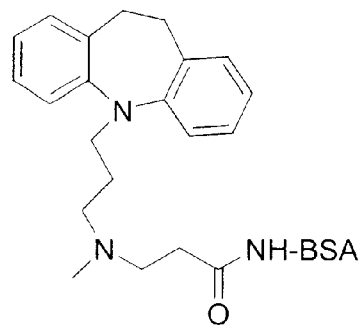
FIG. 6 illustrates the structures for compounds 27, 28, 29 and 30.
Figure 6:
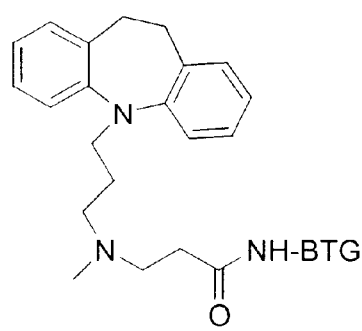
Figure 6:
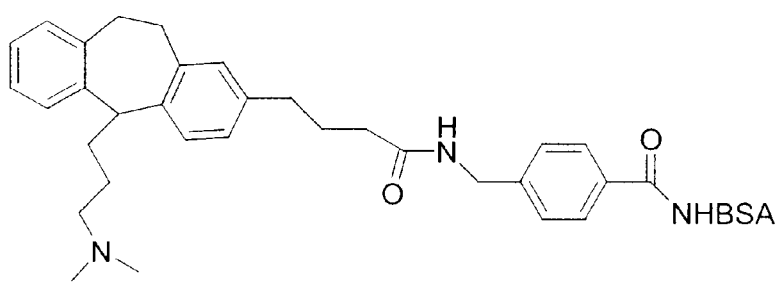
Figure 6:
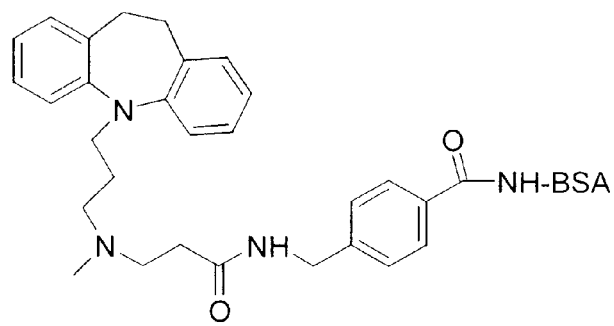
Figure 7:
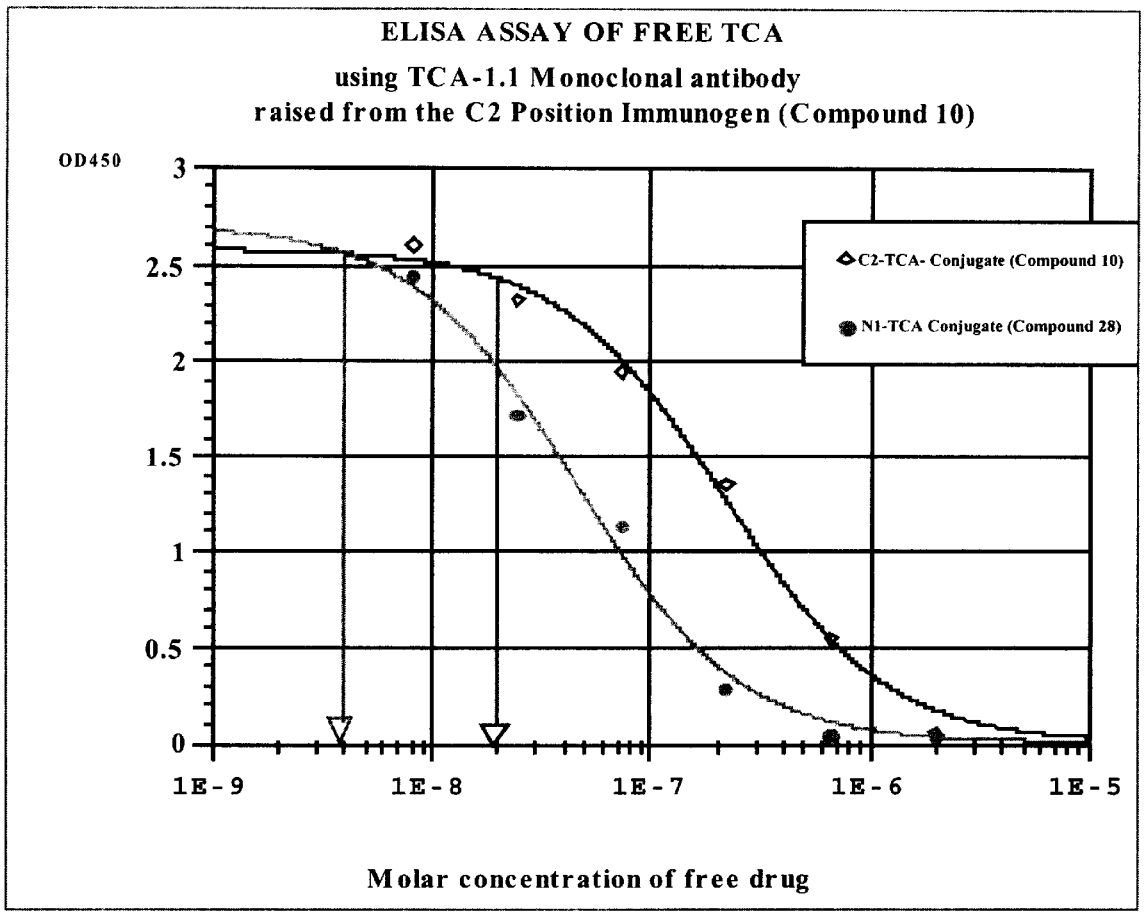
FIG. 7 is a graph showing standard (dose response) curves generated from data obtained using conjugates and antibodies of the present invention in a microwell plate based enzyme immunoassay.

Calibration material means any standard or reference material containing a known amount of the analyte to be measured. The sample suspected of containing the analyte and the calibration material are assayed under similar conditions. Analyte concentration is then calculated by comparing the results obtained for the unknown specimen with results obtained for the standard. This is commonly done by constructing a calibration curve such as in FIGS. 6 and 7.

Various ancillary materials will frequently be employed in an assay in accordance with the present invention. For example, buffers will normally be present in the assay medium, as well as stabilizers for the assay medium and the assay components. Frequently, in addition to these additives, additional proteins may be included, such as albumin, or surfactants, particularly non-ionic surfactants, or the like.

Another aspect of the present invention relates to kits useful for conveniently performing the assay methods of the invention for the determination of an analyte. To enhance the versatility of the subject invention, reagents useful in the methods of the invention can be provided in packaged combination, in the same or separate containers, in liquid or lyophilized form so that the ratio of the reagents provides for substantial optimization of the method and assay. The reagents may each be in separate containers or various reagents can be combined in one or more containers depending on the cross-reactivity and stability of the reagents.

The present invention also encompasses a reagent test kit which comprises, in packaged combination, an antibody specific for imipramine, desipramine, amitriptyline, or nortriptyline, a complex comprising a ligand of a TCA derivative coupled to a labeling moiety, and may optionally also comprise one or more calibrators comprising a known amount of a substance selected from the group consisting of imipramine, desipramine, amitriptyline and nortriptyline. Such a test kit provides reagents for an assay with enhanced clinical sensitivity for imipramine, desipramine, amitriptyline, nortriptyline and structurally-related compounds.

In the examples that follow, boldface numbers refer to the corresponding structure in the drawings.

Example 1

Preparation of 3-(3-methoxy-benzylidene)-3H-isobenzofuran-1-one (1)

A mixture of 15 g (89 mmol) of m-methoxyphenyl acetic acid, 13.2 g (89 mmol) of phthalic anhydride and 246 mg (2.9 mmol) of sodium acetate was heated to 240° C. for 6 hours and water was continuously removed from the reaction. The solid formed in the reaction flask on cooling. This was recrystallized from absolute ethanol to obtain 15.6 g (62 mmol, 69%) of 1 as yellow powder.

Example 2

Preparation of 2-[2-(3-methoxy-phenyl)-ethyl]-benzoic Acid (2)

A solution of 15.6 g of 1 (62 mmol) in 300 ml of THF was added 30 g of 10% Pd-C, 40 g of ammonium formate and 17.2 ml of triethyl amine. The reaction mixture was heated at 70° C. for 6 hours and filtered. The filtrate was concentrated and redissolved in 500 ml of ethyl acetate and washed with 2×150 ml of 3% aqueous HCl and 2×100 ml of brine. The organic layer was concentrated and triturated with 1:1 ethyl acetate:hexane to give 8 g (31.2 mmol, 51%) of 2.

Example 3

Preparation of 2-methoxy-10,11-dihydro-dibenzo[a,d]cyclohepten-5-one (3)

To 5 g of phosphorous pentoxide was added 50 ml of methane sulphonic acid. The mixture was heated to 80° C. for 1 hour. The reaction mixture was brought down to 40° C. and 3 g (11.7 mmol) of 2 was added as solid. The mixture was heated at 40° C. for 1 hour and cooled down to room temperature. The reaction mixture was poured into 300 ml of ice/water and extracted with 200 ml of ethyl acetate. The organic layer was washed with 2×150 ml of water, 2×150 ml of saturated $NaHCO_3$ and 100 ml of water. The resulting organic layer was dried ($Na_2SO_4$) and concentrated to give 2.6 g (11.7 mmol, 94%) of 3 as off-white powder.

Example 4

Preparation of 5-(3-dimethylamino-propyl)-2-methoxy-10,11-dihydro-5H-dibenzo[a,d]cyclohepten-5-ol (4)

To 30 g of magnesium turnings was added 100 ml of freshly distilled THF and a catalytic amount of iodine. The reaction mixture was heated to reflux for 10 minutes and cooled to room temperature. To this reaction mixture 3.5 g (29 mmol) of 3-chloro-N,N-dimethylpropane was added and the reaction mixture was heated to reflux for 3 hours. The reaction mixture was cooled to room temperature and a solution of 2 g of 3 (8.3 mmol) in 20 ml of freshly distilled THF was added. The reaction was allowed to stir at room temperature for 2 hours and filtered. To the filtrate 10 ml of saturated solution of ammonium chloride was added and concentrated to remove THF. This was diluted with 100 ml of saturated ammonium chloride and extracted with ethyl acetate (3×150 ml). The combined organic layer was washed with 2×75 ml of saturated $NaHCO_3$ and 2×75 ml of water, dried ($Na_2SO_4$) and concentrated. The crude product was purified by silica gel column chromatography using 10% methanol in dichloromethane to give 2.6 g (7.9 mmol, 95%) of 4 as white powder.

Example 5

Preparation of 10,11-dihydro-2-methoxy-N,N-dimethyl-5H-dibenzo[a,d]cyclohepten-5-propylamine (5)

To 65 mg (0.19 mmol) of 4 was added 5 ml of glacial acetic acid. The mixture was heated to 60° C. and allowed to stir until the mixture was homogeneous. The reaction mixture was cooled to room temperature and 300 mg of 10% Pd/C was added followed by 1 g of ammonium formate. The mixture was heated to 70° C. and allowed to stir at that temperature for 4 hours. The reaction mixture was cooled to room temperature and filtered. The residue was washed with 50 ml of dichloromethane. The combined filtrate was concentrated. The residue was dissolved in 100 ml of dichloromethane and washed with 2×50 ml of saturated $NaHCO_3$ followed by 2×50 ml of brine. The organic part was dried ($Na_2SO_4$) and concentrated to give 50 mg (0.16 mmol, 82%) of 5.

Example 6

5-(3-dimethylaminopropyl)-10,11-dihydro-5H-dibenzo[a,d]cyclohepten-2-ol Hydrobromide (6)

To 35 ml of freshly distilled dichloromethane was added 1.98 ml of boron tribromide. The reaction mixture was placed in a water bath. To the reaction mixture was added a solution of 1.1 g (3.5 mmol) of 5 in 15 ml of dichloromethane dropwise. The mixture was allowed to stir at room temperature (23–26° C.) for 30 minutes and poured into 50 g of ice/water. An additional 50 ml of water was added and extracted with 3×100 ml of chloroform. The combined organic layer was dried ($Na_2SO_4$) and concentrated to give 1.2 g (3.18 mmol, 90%) of 6 as an off-white solid.

Example 7

Preparation of 4-[5-(3-dimethylaminopropyl)-10,11-dihydro-5H-dibenzo[a,d]cyclohepten-2-yloxy]-butyric Acid Ethyl Ester (7)

To 500 mg (1.32 mmol) of 6 was added 10 ml of freshly distilled acetone (distilled over anhydrous $K_2CO_3$) and 10 ml of anhydrous DMF. To this reaction mixture was added 450 mg (3.0 mmol) of sodium iodide, 2 g of 4° A molecular sieves, 2 g (6.13 mmol) of cesium carbonate and a catalytic amount of 18-crown-6. To this reaction mixture was added 500 µl (3.38 mmol) of ethyl 4-bromobutyrate and the reaction mixture was heated on an preheated oil bath (90° C.) under argon atmosphere for 18 hours. The mixture was cooled to room temperature and filtered. The residue was washed with 30 ml of chloroform. The combined filtrate was concentrated under reduced pressure and redissolved in 100 ml of dichloromethane. This was washed with 2×100 ml of 5% NaOH followed by 2×100ml of water, dried ($Na_2SO_4$) and concentrated. The residue was purified by silica gel column chromatography using 10% methanol in dichloromethane to give 450 mg (1.09 mmol, 83%) of 7 as a brownish oil.

Example 8

Preparation of 4-[5-(3-dimethylamino-propyl)-10,11-dihydro-5H-dibenzo[a,d]cyclohepten-2-yloxy]-butyric Acid (8)

To a solution of 875 mg of 7 (2.1 mmol) in 10 ml of freshly distilled THF was added a solution of 875 mg of lithium hydroxide in 10 ml of water and 5 ml of methanol. The reaction was allowed to stir at room temperature 18 hours and concentrated to remove THF and methanol. The aqueous residue was adjusted to pH 6 with 6N HCl. This was extracted with 3×100 ml of dichloromethane. The pH of the aqueous part was readjusted to 6 again after first extraction. The combined organic part was dried ($Na_2SO_4$) and concentrated to give 790 mg (2.0 mmol, 97%) of 8 as white amorphous solid.

Example 9

Preparation of 4-[5-(3-dimethylamino-propyl)-10,11-dihydro-5H-dibenzo[a,d]cyclohepten-2-yloxy]-butyric acid 2,5-dioxo-pyrrolidin-1-yl Ester (9)

To a solution of 200 mg (0.52 mmol) of 8 in 40 ml of dichloromethane (distilled over calcium hydride) was added 92 mg (0.8 mmol) of N-hydroxysuccinimide and 152 mg (0.8 mmol) of 1-ethyl-3-(3-dimethylaminopropyl) carbodiimide hydrochloride (EDC). The reaction mixture was allowed to stir at room temperature for 48 hours. The reaction mixture was diluted with 50 ml of dichloromethane and washed with 50 ml of brine, 2×50 ml of saturated sodium bicarbonate followed by 2×50 ml of brine. The resulting solution was dried ($Na_2SO_4$) and concentrated to give 245 mg (0.51 mmol, 98%) of 9 as a white solid.

Example 10

Preparation of C-2 position TCA Immunogen (10)

To 738 mg of bovine thyroglobulin in 12 ml of 50 mM potassium phosphate (pH 7.5) was cooled in an ice-bath. To the solution was added 37 ml of dimethylsulfoxide dropwise and the reaction temperature was maintained below room temperature. To the protein solution was added a solution of 111 mg (0.23 mmol) of 9 in 1 ml of DMF dropwise. The mixture was allowed to stir at room temperature 18 hours. The resulting conjugate was placed in a dialysis tube (50,000 MW cut-off) and was dialyzed in 2 L of 70% DMSO in 50 mM potassium phosphate (pH 7.5, 3 changes, at least 3 hours each), 2 L of 50% DMSO in 50 mM potassium phosphate (at least 3 hours), 2 L of 30% DMSO in 50 mM potassium phosphate (at least 3 hours), 10% DMSO in 50 mM potassium phosphate (at least 3 hours) at room temperature followed by 6 changes with 50 mM potassium phosphate (pH 7.5) at 4° C. (2 L each for at least 6 hours each). The protein concentration was determined to be 3.9 mg/ml using Biorad Coomassie blue protein assay (Bradford, M., *Anal. Biochem.* 72, 248, 1976). A total of 100 ml of the conjugate was obtained. The extent of available lysine modification was determined to be 70% by the TNBS method (Habeeb AFSA, *Anal. Biochem.* 14, 328–34, 1988).

Example 11

Preparation of C-2 position TCA-BSA ELISA Screening Conjugate (11)

A solution of 1 g of bovine serum albumin (BSA) in 16 ml of 50 mM potassium phosphate (pH 7.5) was cooled in an ice-bath. To the solution was added 19 ml of DMSO dropwise and the reaction temperature was maintained below room temperature. To the protein solution was added a solution of 18.1 mg (0.038 mmol) of C-2 position TCA NHS ester derivative (9) in 1.5 ml of anhydrous DMF dropwise. The reaction mixture was allowed to stir at room temperature 48 hours. The resulting conjugate was placed in a dialysis tube (10,000 MW cut-off) and was dialyzed in 2 L of 60% DMSO in 50 mM potassium phosphate (3 changes, at least 3 hours each), 2 L of 50% DMSO in 50 mM potassium phosphate (at least 3 hours), 2 L of 30% DMSO in 50 mM potassium phosphate (at least 3hours), 2 L of 10% DMSO in 50 mM potassium phosphate (at least 3 hours) at room temperature followed by 6 changes with 50 mM potassium phosphate (pH 7.5) at 4° C. (2 L each for at least 6 hours each). A total of 70 ml of TCA-BSA conjugate was obtained. The protein concentration was determined to be 8.2 mg/ml using Biorad Coomassie blue protein assay. Overall drug:BSA ratio=2.5:1.

Example 12

Preparation of 4-[5-(3-dimethylaminopropyl)-10,11-dihydro-5H-dibenzo[a,d]cyclohepten-2-yloxymethyl]benzoic Acid Methyl Ester (12)

A solution of 100 mg (0.34 mmol) of hydroxy TCA derivative 6 in 3 ml of DMF under argon was treated with 16 mg (0.4 mmol) of NaH (60% dispersion in mineral oil) and stirred at room temperature for 15 minutes. The mixture was then treated with 85 mg (0.37 mmol) of methyl-4-(bromomethyl) benzoate and stirred at room temperature for 4 hours. The reaction diluted with $CH_2Cl_2$ and washed with 50 mM $KPO_4$, pH 7. The aqueous portion was extracted once with $CH_2Cl_2$. The combined $CH_2Cl_2$ portions were dried over $Na_2SO_4$ and concentrated in vacuo to an oil. This was chromatographed on 20 g of silica gel using 3% MeOH in $CH_2Cl_2$ as eluent to yield 46 mg (31%) of 12 as a pale yellow oil.

Example 13

Preparation of 4-[5-(3-dimethylaminopropyl-10,11-dihydro-5H-dibenzo[a,d]cyclohepten-2-yloxymethyl]benzoic Acid (13)

A solution of 46 mg (0.104 mmol) of 12 in 4.5 ml of MeOH and 0.5 ml of $H_2O$ under argon was treated with 28 mg (0.202 mmol) of $K_2CO_3$ and heated to reflux for 4 hours. The reaction was concentrated in vacuo. The residue was dissolved in $H_2O$ and the pH adjusted to 6.5 with dilute HCl. A precipitate formed. This was extracted with 3×10 ml of $CH_2Cl_2$, dried over $Na_2SO_4$ and concentrated in vacuo to yield 35 mg (79%) of 13 as an off-white amorphous solid.

Example 14

Preparation of 4-[5-(3-dimethylaminopropyl)-10,11-dihydro-5H-dibenzo[a,d]cyclohepten-2-yloxymethyl]benzoic acid 2,5-dioxo-pyrrolidin-1-yl Ester A solution of 35 mg (0.082 mmol) of acid 13 in 5 ml of $CH_2Cl_2$ under argon was treated with 25 mg (0.217 mmol) of N-hydroxysuccinimide and 40 mg (0.209 mmol) of 1-ethyl-3-(3-dimethylaminopropyl)carbodiimide HCl and stirred at room temperature overnight. The reaction was washed with $H_2O$, saturated $NaHCO_3$ and brine, dried over $Na_2SO_4$ and concentrated in vacuo to give 30 mg (70%) of 14 as a white amorphous solid.

Example 15

Preparation of 4-({4-[5-(3-dimethylaminopropyl)-10,11-dihydro-5H-dibenzo[a,d]cyclohepten-2-yloxy]butyrylamino}methyl)benzoic Acid (15)

A mixture of 32 mg (0.212 mmol) of 4-(aminomethyl)benzoic acid in 2 ml of $H_2O$ and 4 ml of THF was treated with approximately 0.1 ml of 2 N NaOH such that the pH of the mixture was about 9. This was then treated with a solution of 100 mg (0.209 mmol) of the TCA NHS ester 9 in 4.5 ml of THF. The pH was adjusted to about 8.5–9.0 with 2 N NaOH and the reaction was stirred at room temperature for 15 minutes. The reaction was neutralized to pH 6 with 2 N HCl, then extracted twice with $CH_2Cl_2$. The $CH_2Cl_2$ portions were combined, dried over anhydrous $Na_2SO_4$ and concentrated in vacuo to give 87 mg (81%) of the acid 15 as a pale yellow oil. This was used in the next step without further purification.

Example 16

Preparation of 4-({4-[5-(3-dimethylaminopropyl)-10,11-dihydro-5H-dibenzo[a,d]cyclohepten-2-yloxy]butyrylamino}methyl)benzoic acid 2,5-dioxo-pyrrolidin-1-yl Ester (16)

A solution of 87 mg (0.169 mmol) of the acid (15) in 10 ml of $CH_2Cl_2$ was treated with 40 mg (0.348 mmol) of N-hydroxysuccinimide and 87 mg (0.454 mmol) of 1-ethyl-3-(3-dimethylaminopropyl)carbodiimide HCl and stirred at room temperature overnight. The reaction was washed with $H_2O$, saturated $NaHCO_3$ and brine, dried over $Na_2SO_4$ and concentrated in vacuo. The residue was chromatographed on silica gel using 10% ether in $CH_2Cl_2$ as eluent to give 34 mg (33%) of 16 as a white amorphous solid.

Example 17

Preparation of 3-{[3-(10,11-dihydro-dibenzo[b,f]azepine-5-yl)-propyl]-methyl-amino}-propionic Acid Ethyl Ester (17)

A solution of 6.02 g (19.8 mmol) of desipramine hydrochloride was allowed to stir at room temperature for 5 minutes. This was extracted with 6×100 ml of chloroform. The combined organic part was washed with 100 ml of water, dried with anhydrous $Na_2SO_4$ and concentrated to give 5.25 g of desipramine free base. A solution of 2.82 g (10.6 mmol) of desipramine free base in 100 ml of anhydrous acetone was added. To this reaction mixture 2.03 ml (15.8 mmol) of ethyl-3-bromopropionate, 3.65 g (26.4 mmol) of anhydrous potassium carbonate, 264 mg (1.76 mmol) of sodium iodide, 5 mg of 18-crown-6 and 0.7 ml of anhydrous DMF were added. The reaction mixture was allowed to reflux under argon overnight. The mixture was filtered and the residue was washed with 20 ml of acetone. The combined filtrate was concentrated and purified by silica gel column chromatography using 4% methanol in ethyl acetate to give 3.45 g (9.41 mmol, 89%) of the ethyl ester (17) as a thick oil.

Example 18

Preparation of 3-3{[3-(10,11-dihydro-dibenzo[b,f]azepin-5-yl)-propyl]-methyl-amino}-propionic Acid (18)

To 2.15 g (5.86 mmol) of the ethyl ester (17) was added 29.6 ml of freshly distilled THF, 29.6 ml of methanol and a solution of 4.7 g of lithium hydroxide in 63 ml of water. This mixture was allowed to stir at room temperature overnight and concentrated to remove methanol and THF. The pH of the aqueous solution was adjusted to 6. This was extracted with 6×100 ml of chloroform. The combined organic layers were washed with 100 ml of water, dried (anhydrous $Na_2SO_4$) and concentrated to give 1.97 g (5.82 mmol, 99%) of 18 as white amorphous solid.

Example 19

Preparation of 4-[(3-{[3-(10,11-dihydro-dibenzo[b,f] azepin-5-yl)-propyl]-methyl-amino}-propionylamino)-methyl]-benzoic Acid Methyl Ester (19)

To a solution of 0.93 g (2.74 mmol) of 18 in 100 ml of anhydrous dichloromethane was added 446 mg (2.21 mmol) of methyl aminomethyl benzoate hydrochloride (20) followed by 1.05 g (5.47 mmol) 1-ethyl-3-(3-dimethylaminopropyl)-carbodiimide. The mixture was allowed to stir at room temperature overnight. To the reaction mixture was added 100 ml of water and 20 ml of dichloromethane. The organic layer was separated and the aqueous part was extracted with 4×75 ml of dichloromethane. The combined organic layer was washed with 2×100 ml of water, dried ($Na_2SO_4$) and concentrated. The above reaction was repeated using 1.02 g of 18. The combined crude product was purified by silica gel column chromatography using 30% chloroform in methanol to give 1.2 g (2.47 mmol, 43%) of the methyl ester (19). An additional 760 mg of the product was also obtained containing small impurities.

Example 20

Preparation of Methylaminomethyl Benzoate Hydrochloride (20)

A magnetically stirred suspension of 6.05 g (40 mmol) of aminomethyl benzoic acid in 480 ml of methanol was cooled to −20° C. To the reaction mixture 12.3 ml of thionyl chloride was added for a period of 10 minutes. The reaction mixture was warmed up to 4° C. and was allowed to stir at that temperature overnight. The resulting solution was concentrated to give a solid. NMR analysis indicated that the reaction was not complete. This was again subjected to the above reaction conditions to give 7.8 g (38 mmol, 96%) of 20 as an off-white solid.

Example 21

Preparation of 4-[(3-{[3-(10,11-dihydro-dibenzo[b,f] azepin-5-yl)-propyl]-methyl-amino}-propionylamino)-methyl]-benzoic Acid (21)

To 1.2 g (2.47 mmol) of 18 were added 16.5 ml of THF, 16.5 ml of methanol and a solution of 2.63 g of lithium hydroxide in 38 ml of water. The mixture was allowed to stir at room temperature overnight. This was concentrated to remove methanol and THF. The pH of the solution was adjusted to 6 using 85% phosphoric acid. The resulting mixture was extracted with 5×100 ml of chloroform. The combined organic layer was washed with 100 ml of water, dried ($Na_2SO_4$) and concentrated. The residue was purified twice by silica gel column chromatography using 7:3 methanol:ethyl acetate to give 550 mg (1.16 mmol, 47%) of 21.

Example 22

Preparation of 4-[3-{[3-(10,11-dihydro-dibenzo[b,f] azepin-5-yl)-propyl]-methyl-amino)-methyl-]benzoic acid 2,5-dioxo-pyrrolidin-1-yl Ester (22)

A solution of 55 mg (1.16 mmol) of 21 in 30 ml of dichloromethane was allowed to stir at room temperature under argon atmosphere. To the reaction mixture was added 575 mg (2.9 mmol) of 1-ethyl-3(3-dimethylaminopropyl)-carbodiimide) and 264 mg (2.29 mmol) of N-hydroxysuccinimide. The mixture was allowed to stir for 24 hours and was diluted with 15 ml of dichloromethane. The organic layer was separated and washed with 4×50 ml of water, 3×50 ml of saturated $NaHCO_3$ solution and 3×50 ml of water. The dichloromethane layer was dried ($Na_2SO_4$) and concentrated to give 480 mg (0.8 mmol, 72%) of 22 as a white powder.

Example 23

Preparation of {2-[3-(10,11-Dihydro-dibenzo[b,f] azepin-5-yl)-propylamino]-ethyl]-carbamic Acid tert-butyl Ester (23)

To 6.02 g of desipramine hydrochloride was added 150 ml of 1N NaOH. The mixture was allowed to stir for 10 minutes. The aqueous mixture was extracted with 6×100 ml of chloroform. The combined chloroform layer was washed with 200 ml of water. The organic part was dried ($Na_2SO_4$) and concentrated to give 5.25 g of desipramine free base.

To 3.23 g (12.04 mmol) of desipramine free base was added 80 ml of dry acetone, 3.6 g of anhydrous potassium carbonate, 3.0 g (13.45 mmol) of 2-(BOC-amino) ethyl bromide, 3 ml of anhydrous dimethylformamide, 15 mg of 18-crown-6 and 500 mg of sodium iodide. The mixture was allowed to reflux 18 hours under argon atmosphere. The reaction mixture was cooled to room temperature and filtered. The residue was washed with 10 ml of acetone. The filtrate was concentrated and the residue was purified by silica gel column chromatography using 4% methanol in ethyl acetate to give 4.8 g (11.7 mmol, 96%) of 23 as a thick oil.

Example 24

Preparation of N-[3-(10,11-Dihydro-dibenzo[b,f] azepin-5-yl)-N1-methyl-ethane-1,2-diamine (24)

To 1.0 g (2.44 mmol) of 23 was added 10 ml of CH2Cl2 and 10 ml of trifluoroacetic acid. The reaction mixture was allowed to stir at room temperature and concentrated. The residue was dissolved in $CH_2Cl_2$ and concentrated. The above procedure was repeated twice and the residue was purified by silica gel column chromatography using 60% chloroform in methanol to give 1.02 g (2.40 mmol, 99%) of 24 as a thick oil.

Example 25

Preparation of N-(2-{[3-(10,11-Dihydro-dibenzo[b, f]azepin-5-yl)-propyl]-methyl-amino]-ethyl)-terephthalamic acid 2,5-dioxo-pyrrolidin-1-yl Ester (26).

To 500 mg (1.18 mmol) of TCA amine (24) was added 316 μl of triethyl amine and 30 ml of DMF. In a separate flask 1.16 g (mmol) of terephthalic acid di-N-hydroxysuccinimide ester (25) was mixed with 30 ml of anhydrous DMF. The previously prepared TCA amine solution was added to the terephthalic acid di-N-hydroxysuccinimide solution dropwise. The reaction mixture was allowed to stir at room temperature overnight and concentrated. The residue was dissolved in 75 ml of dichloromethane. The organic layer was washed with 2×50 ml of water, 2×50 ml of saturated solution of $NaHCO_3$ and 50 ml of water, dried ($Na_2SO_4$) and concentrated. The residue was purified by silica gel column chromatography using 20% acetone in ethyl acetate to give 145 mg (0.26 mmol, 22%) of 26 as white powder.

Example 26

Preparation of N-1 position TCA Immunogen (28)

A solution of 96 mg of TCA NHS ester derivative (18) in 1.5 ml of anhydrous DMF was cooled to 0° C. To the reaction mixture was added 74 mg of dicyclohexyl urea (DCC) and 48 mg of N-hydroxysuccinimide. The mixture was allowed to stir at 4° C. for 24 hours. The N-hydroxysuccinimide ester prepared was used in situ in the protein conjugation.

Seven hundred mg of bovine thyroglobulin in 12 ml of 50 mM potassium phosphate (pH 7.5) was cooled in an ice-bath. To the solution was added 37 ml of dimethylsulfoxide (DMSO) dropwise and the reaction temperature was maintained below room temperature. To the protein solution was added dropwise the N-hydroxysuccinimide ester solution prepared in situ (as described above). The mixture was allowed to stir at room temperature 18 hours. The resulting conjugate was placed in a dialysis tube (50,000 MW cut-off) and was dialyzed in 2 L of 70% DMSO in 50 mM potassium phosphate (pH 7.5, 3 changes, at least 3 hours each), 2 L of 50% DMSO in 50 mM potassium phosphate (at least 3 hours), 2 L of 30% DMSO in 50 mM potassium phosphate (at least 3 hours), 10% DMSO in 50 mM potassium phosphate (at least 3 hours) at room temperature followed by 6 changes with 50 mM potassium phosphate (pH 7.5) at 4° C. (2 L each for at least 6 hours each). The protein concentration was determined to be 4.5 mg/ml using Biorad Coomassie blue protein assay (Bradford, M., *Anal. Biochem.* 72, 248 (1976). A total of 90 ml of the conjugate (28) was obtained. The extent of available lysine modification was determined to be 70% by the TNBS method, Habeeb AFSA, *Anal. Biochem.* 14, 328–34 (1988). Note: Reference for preparation of protein conjugate: Hubbard et al., *J. Pharm. Sc.* 67, 1571–1578 (1978).

Example 27

Preparation of C-2 position TCA-BSA (aromatic linker) Conjugate (29)

A solution of 550 mg of bovine serum albumin (BSA) in 11 ml of 50 mM potassium phosphate (pH 7.5) was prepared. A 10 ml solution was transferred into a RB flask and cooled in an ice-bath. To the solution was added 10 ml of DMSO dropwise and the reaction temperature was maintained below room temperature. To the protein solution was added a solution of 48.2 mg of C-2 position TCA NHS ester derivative (16) in 0.96 ml DMSO dropwise. The reaction mixture was allowed to stir at room temperature 16 h. The resulting conjugate was placed in a dialysis tube (10,000 MW cut-off) and was dialyzed against 500 ml of 50% DMSO in 50 mM potassium phosphate (at least 3 hours at room temperature), 500 ml of 30% DMSO in 50 mM potassium phosphate (at least 3 h at room temperature), 500 ml of 10% DMSO in 50 mM potassium phosphate (at least 3 h at room temperature) followed by 4 changes with 50 mM potassium phosphate (pH 7.5) at 4° C. (2 L each for at least 3 hours each). The resulting conjugate was filtered through a 0.45 µm filter. A total of 37 ml of TCA-BSA conjugate was obtained. The protein concentration was determined to be 14.4 mg/ml using Biorad Coomassie blue protein assay.

Example 28

Preparation of N-1-position TCA-BSA (aromatic linker) Conjugate (30)

A solution of 1 g of bovine serum albumin (BSA) in 16 ml of 50 mM potassium phosphate (pH 7.5) was cooled in ice-bath. To the solution was added 19 ml of DMSO dropwise and the reaction temperature was maintained below room temperature. To the protein solution was added a solution of 21 mg of TCA NHS ester derivative (22) in 1.5 ml of anhydrous DMF dropwise. The reaction mixture was allowed to stir at room temperature 24 h. The resulting conjugate was placed in a dialysis tube (10,000 MW cut-off) and was dialyzed in 2 L of 60% DMSO in 50 mM potassium phosphate (3 changes, at least 3 hours each), 2 L of 50% DMSO in 50 mM potassium phosphate (at least 3 h), 2 L of 30% DMSO in 50 mM potassium phosphate (at least 3 h), 2 L of 10% DMSO in 50 mM potassium phosphate (at least 3 h) at room temperature followed by 6 changes with 50 mM potassium phosphate (pH 7.5) at 4° C. (2 L each for at least 6 hours each). A total of 75 ml of TCA-BSA conjugate was obtained. The protein concentration was determined to be 11.4 mg/ml using Biorad Coomassie blue protein assay.

Example 29

Preparation of N-1-position TCA-BSA (short linker) Conjugate (27)

A solution of 12.8 mg of TCA NHS ester derivative (18) in 1.5 ml of anhydrous DMF was cooled to 0° C. To the reaction mixture was added 9.3 mg of dicyclohexyl urea (DCC) and 5.24 mg of N-hydroxysuccinimide. The mixture was allowed to stir at 4° C. for 24 h. The N-hydroxysuccinimide ester prepared was used in situ in the protein conjugation.

A solution of 1 g of bovine serum albumin (BSA) in 16 ml of 50 mM potassium phosphate (pH 7.5) was cooled in ice-bath. To the solution was added 19 ml of DMSO dropwise and the reaction temperature was maintained below room temperature. To the protein solution was added dropwise the N-hydroxysuccinimide ester solution prepared in situ (as described above). The reaction mixture was allowed to stir at room temperature 24 h. The resulting conjugate was placed in a dialysis tube (10,000 MW cut-off) and was dialyzed in 2 L of 60% DMSO in 50 mM potassium phosphate (3 changes, at least 3 hours each), 2 L of 50% DMSO in 50 mM potassium phosphate (at least 3 h), 2 L of 30% DMSO in 50 mM potassium phosphate (at least 3 h), 2 L of 10% DMSO in 50 mM potassium phosphate (at least 3 h) at room temperature followed by 6 changes with 50 mM potassium phosphate (pH 7.5) at 4° C. (2 L each for at least 6 hours each). A total of 100 ml of TCA-BSA conjugate was obtained. The protein concentration was determined to be 7.2 mg/ml using Biorad Coomassie blue protein assay.

Example 30

Development of Polyclonal Antisera to the C-2 Position Immunogen

Healthy, previously un-immunized rabbits of either sex were chosen for this work. Rabbits were housed and treated as approved by the vendor's IUACUC committee.

Primary immunization was with the 2-carboxypropyl-dihydroamitriptyline-BTG conjugate emulsified in complete Freund's adjuvant at a concentration of 1 mg/ml. Total dose administered to each rabbit was 0.2 ml or 0.2 mg, delivered by subcutaneous injection at multiple sites across the back. Four weeks later the immunization was repeated, substituting incomplete Freund's adjuvant, at different sites across the back, again via subcutaneous injection. Immunizations were then repeated at four-week intervals, using a total dose of 0.1 mg, administered via the same route as previously described, to week 16.

Antibody response was determined via ELISA of samples taken via ear vein bleeds. Serial dilutions of clarified serum were tested on both the C-2 position and N-1 position test protein (BSA) conjugates. The titers of the sera, expressed as the 50% of maximal response dilution, were generally similar with respect to the test conjugate used, approximately 5×10$^5$. Variations appeared to be more related to the individual animal than to the conjugate used for testing, in that high responders on the C-2 position test conjugate also were higher on the N-1 position conjugate, and the order of response among the animals, from highest to lowest, was generally the same as measured on each test conjugate.

Example 31

Immunization of Mice with C-2 Immunogen

The C-2 immunogen, compound 10, was prepared for primary immunization of mice by diluting to 0.2 mg/ml in physiological saline and emulsifying with an equal volume of Freund's Complete Adjuvant (Sigma Chemicals, St Louis, Mo.) by using two syringes and a double-hubbed 25 gauge needle. The emulsion was injected into the mice in each rear footpad and into the peritoneal area. A total dose of 0.1 ml per mouse was injected. A secondary injection using the same formulation with Freund's Incomplete Adjuvant was injected via the same routes four weeks later. The third injection was the same as the second and was administered 6 weeks following the second injection.

Blood samples were taken via retro-orbital bleeding 14 days after the second injection. Serum was separated via centrifugation and preserved via the addition of 1 μl of 10% thimerosal solution. The typical volume of serum was 10–20 μl.

Example 32

ELISA assay

To analyze the sera for antibody content an ELISA assay using the cognate antigen linked to a different protein (2-carboxypropyl-dihydroamitriptyline-BSA) (compound 11) was used. This antigen was diluted to 5 μg/ml in 0.1 M carbonate buffer, pH 9.5. A volume of 100 μl of this antigen solution was pipetted into wells of a polystyrene 96-well microplate (Costar, Cambridge, Mass.). This was incubated in a plastic bag at 37° C. for 1 hour. The solutions were then removed via suction, and wells were filled with a blocking solution. This consisted of gelatine hydrolysate, 1%, sucrose, 2%, Tris, 0.15 M, pH 7.4 (all reagents from Sigma Chemicals). This was allowed to block the plates for 1 hour at room temperature in plastic bags. Wells were then emptied via suction.

Dilutions of the sera were prepared by transferring 1 μl to a glass test tube containing 1 ml of phosphate buffered saline, with 0.1% Tween 20 (PBS-T). One hundred and fifty microliters of this dilution of each serum were transferred to wells in Row A of a polyvinyl chloride microplate. All other wells were filled with 100 μl of PBS-T. Serial three-fold dilutions were prepared by transferring 50 μl from Row A to Row B using a multi-channel micropipettor. Mixing was accomplished by re-pipetting 3 times. This was repeated from Row B to C and so on down each column of wells.

Once all dilutions were prepared, 95 μl of each, starting with Row H, was transferred to the same row in the coated plate. The plate was placed in a Ziploc plastic bag with a damp piece of paper towel and incubated at 37° C. for one hour. Following incubation, the wells were washed four times manually with 300 μl aliquots of PBS-T. A 1:5000 dilution of goat anti-mouse IgG AM-HRP conjugate (Kirkegaard & Perry, Gaithersburg, Md.) was prepared in PBS-T. 100 μl of this was then pipetted into each well, the plate again incubated as above. The plate was then washed 6 times with 300 μl of PBS-T manually, and 100 μl of K-Blue substrate (Neogen, Lexington, Ky.) was added to each well. This was allowed to develop in the dark for 5 minutes, and the reaction was then stopped by the addition of 100 μl of a 2 M phosphoric acid solution. The optical densities of the wells were read using a Molecular Devices Tmax plate reader and a Macintosh computer. The data suggested that all mice were sensitized to the immunogen, with some showing more of a response than others.

Example 33

Production of Monoclonal Antibodies from Murine Hybridomas

A mouse showing a high response to the immunogen via ELISA was chosen for use. This animal received a booster immunization of 100 μg of antigen in incomplete Freund's adjuvant four days before the fusion was performed. The myeloma cell line F0 (ATCC, Manassas, Va.) was used for the fusion. The fusion was performed by the method of de St Groth and Scheidegger, *Journal of Immunol. Meth.* 35, 1–21, 1980. Ten days later hybrid cell cultures were ready for screening. This was carried out by a process similar to the ELISA given above, with the addition of plates coated with an N-linked desipramine-BSA conjugate (compound 27) and a control plate coated only with BSA. Hybrid cells showing antibody capable of binding both the compound 11 and compound 27 but not the BS A were chosen for further work. This consisted of immediate re-cloning as well as expansion of the culture for freezing in liquid nitrogen. Re-cloning was carried out by diluting the cells to 60 viable cells per 40 ml of culture media, distribution of 200 μl to each well in sterile 96-well culture plates, and incubation in a humidified $CO_2$ incubator until growth was observed.

Wells of the re-cloning plates showing growth were tested for antibody expression by the screening assay described earlier. Clones showing the desired reactions were expanded and stored in liquid nitrogen.

Monoclonal antibodies were produced by placing the desired hybridoma into tissue culture for expansion of cell number, followed by transfer to standard commercially available culture devices, such as the Miniperm (Hereaus, Germany). Antibody was used as a preserved culture supernatant for assay development.

Example 34

Immunoassay of Imipramine Using Monoclonal Antibody TCA 1.1

Hybridoma clone TCA 1.1 was placed into high-density culture and supernatant harvested. This preparation was preserved by the addition of thimerosal to a concentration of 0.02%. Antibody content was evaluated by a titer experiment in which varying dilutions of supernatant were placed into microplate wells coated with a constant amount of antigen conjugate. The dilution providing about 90% of maximal signal was used for further work in demonstrating an immunoassay.

Imipramine immunoassays were demonstrated by preparing various dilutions of a 1 mg/ml stock solution of the drug in PBS-T. Fifty microliters of these dilutions were pipetted into microplate wells coated with pre-optimized concentrations of either compound 11 or compound 27 conjugates, followed by 50 μl of the antibody supernatant diluted to one half of the previously determined dilution above. This provided a final dilution of supernatant equal to that previously determined and a final concentration of one-half of the drug level in the dilutions above. Incubation for 1 hour at 37° C. was followed by the same procedure as for the screening assays. Optical densities were plotted versus the final concentration of imipramine calculated as a molar (gram-molecular weight drug per liter) concentration. Standard curves with the following data were constructed (see FIG. 7):

TABLE 1

| Imipramine concentration | $OD_{450}$ compound 11 | $OD_{450}$ compound 27 |
|---|---|---|
| $1.98 \times 10^{-6}$ | 0.056 | 0.037 |
| $6.6 \times 10^{-7}$ | 0.541 | 0.038 |
| $2.2 \times 10^{-7}$ | 1.35 | 0.276 |
| $7.43 \times 10^{-8}$ | 1.95 | 1.124 |
| $2.45 \times 10^{-8}$ | 2.325 | 1.719 |
| $8.15 \times 10^{-9}$ | 2.6 | 2.434 |

Based on these results, the lowest detectable amount of free drug by the assay using compound 11 conjugate is estimated to be $1.3 \times 10^{-6}$ M, or approximately 0.36 micrograms per ml. Using the compound 27 conjugate, a lower concentration of $4 \times 10^{-7}$ M, or about 0.11 micrograms/ml, was detectable. Background levels were reproducibly very low, suggesting that incorporation of a longer development time would probably provide lower detectable concentrations.

Furthermore, it was found that the other tricyclic antidepressant drugs also showed cross-reactivity with the binding of TCA 1.1 to both the compound 11 and the compound 27 conjugates. These data support the contention that immunization using the 2-carboxypropyl-dihydroamitriptyline-BTG conjugate (compound 10) is useful in the development of suitable antibodies for the purpose of determining concentrations of tricyclic antidepressants.

Example 35

Absorption of Antibodies to Microparticles

Carboxyl-modified blue polystyrene microparticles from Seradyn (0.3 micron) were first washed three times at 1% solids by centrifuging in 20 mM, pH 6.1 MES buffer (2-[N-morpholino]ethanesulfonic acid). The washed microparticles were then adjusted to 5% solids in MES, and the designated anti-TCA antibody was absorbed onto the microparticles as follows: To the solution of microparticles, an equal volume of 3 mg/ml anti-TCA antibody was added and allowed to stir for 16 hours at room temperature. The microparticles were then blocked with BSA solution in MES for 1 hour at room temperature and the mixture was washed for three times at 1% solids in MES by centrifugation. After the final wash, the microparticle solution was adjusted again to 10% solids. Before use, equal volumes of this latex and 35% w/v sucrose in MES were mixed.

Example 36

Preparation of Membrane Strip

Mylar-backed large pore size nitrocellulose (5–20 micron) was cut into pieces of 15 cm in length and 5 cm in width. Solutions of TCA-BSA conjugate (about 5 mg/ml) and anti-TCA monoclonal antibody (about 2 mg/ml), both in 50 mM potassium phosphate buffer pH 7.5, were dispensed using IVEK Corp. Digispense 2000™ system at the rate 1 µl/cm onto nitrocellulose at a distance respectively 2 cm and 1 cm from the 15 cm side. Nitrocellulose segments were allowed to dry for about 20 minutes at 37° C. and then were blocked with polyvinyl alcohol (PVA, MW 13,000–23,000) solution in 20 mM TRIS, pH 8, for 30 minutes at room temperature. The segments were then rinsed in water and dried.

Example 37

Immunochromatographic Assay of Imipramine using Polyclonal anti-TCA (C-2) Antibody The same nitrocellulose as described above in this example was used as a separate membrane for microparticles (top membrane). The construction of the two-membrane strip configuration was done as described in detail in U.S. Pat. No. 5,770,458. In brief, the top membrane was blocked and washed using the same protocol as the main membrane. The top membrane that contains appropriate amount of microparticles was laminated to the main membrane with Adhesive Research Inc. adhesive mylar. After this, the segment was cut into 5 mm wide strips, sample pad and sink pad were placed respectively at the beginning and terminal ends of the strips. Cellulose from BioRad Laboratories (gel blotter) was used for both the sample receiving pads and the sink pads. A calibration curve was obtained by applying approximately 100 µl solutions containing predetermined amounts of the drug (TCA standards) onto the membrane strip. The signal strength was determined as follows: 2.5 to 3.0=dark blue, 1.5 to 2.0=medium blue, 1.0=light blue, 0.5=barely perceivable color, and 0=colorless. When the strip read colorless, a complete inhibition was achieved and the sample was indicated to contain 1000 ng/ml of TCA standard (e.g., imipramine). Results are presented in Tables 2–5 below and in FIG. 4.

TABLE 2

Figure 8:
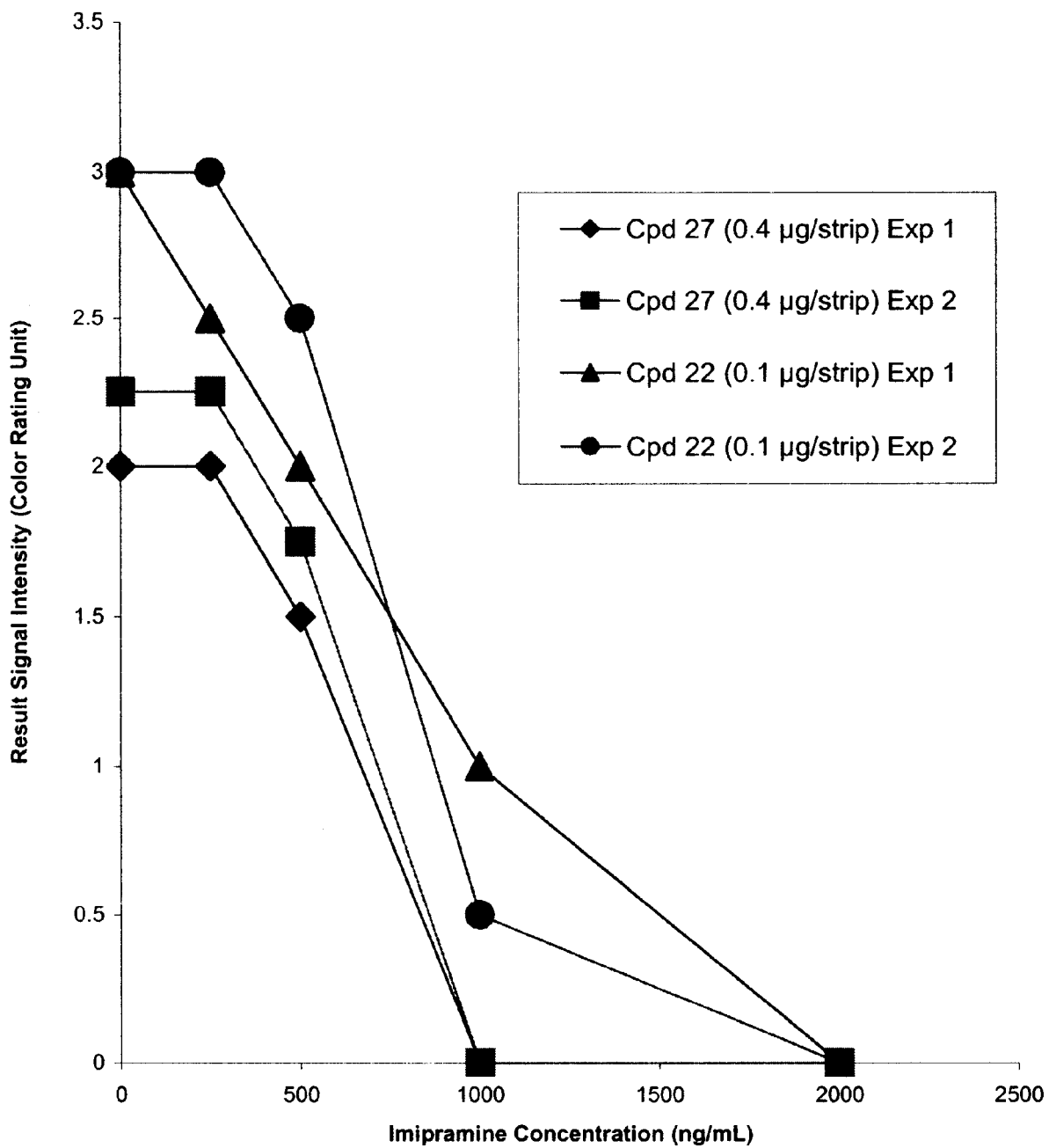
FIGS. 8 and 9 are graphs showing standard (dose response) curves generated from data obtained using conjugates and antibodies of the present invention in a lateral-flow immunoassay.

Presented in Table 2 is the lateral-flow immunoassay standard curve for a TCA assay using compound 27, 0.4 µg/strip, with antibody prepared from the compound 10 immunogen (see FIG. 8).

| Time of testing | Imipramine concentration (ng/ml) | | | | |
|---|---|---|---|---|---|
| | 0 | 250 | 500 | 1000 | 2000 |
| Experiment 1 | 2.00 | 2.00 | 1.50 | 0 | 0 |
| Experiment 2 | 2.25 | 2.25 | 1.75 | 0 | 0 |

TABLE 3

Presented in Table 3 is the lateral-flow immunoassay standard curve for a TCA assay using compound 30, 0.1 µg/strip, with antibody prepared from the compound 10 immunogen (see FIG. 8).

| Time of testing | Imipramine concentration (ng/ml) | | | | |
|---|---|---|---|---|---|
| | 0 | 250 | 500 | 1000 | 2000 |
| Experiment 1 | 3.00 | 2.50 | 2.00 | 1.00 | 0.50 |
| Experiment 2 | 3.00 | 3.00 | 2.50 | 0.50 | 0 |

TABLE 4

Figure 9:
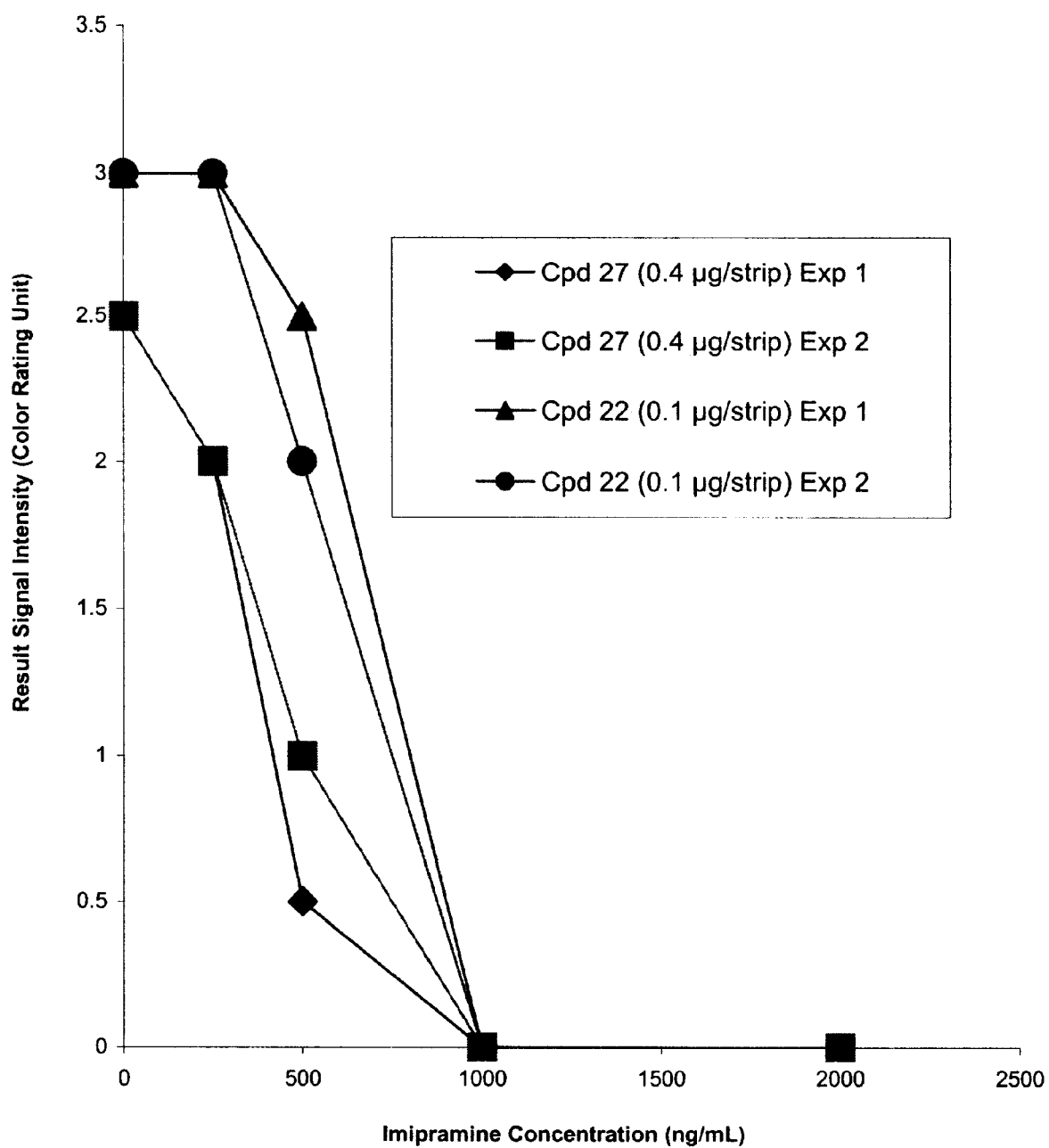

Presented in Table 4 is the lateral-flow immunoassay standard curve for a TCA assay using compound 27, 0.4 μg/strip, with antibody prepared from the compound 28 immunogen (see FIG. 9).

| Time of testing | Imipramine concentration (ng/ml) | | | | |
| --- | --- | --- | --- | --- | --- |
|  | 0 | 250 | 500 | 1000 | 2000 |
| Experiment 1 | 2.50 | 2.00 | 0.50 | 0 | 0 |
| Experiment 2 | 2.50 | 2.00 | 1.00 | 0 | 0 |

TABLE 5

Presented in Table 5 is the lateral-flow immunoassay standard curve for a TCA assay using compound 30, 0.1 μg/strip, with antibody prepared from the compound 28 immunogen (see FIG. 9).

| Time of testing | Imipramine concentration (ng/ml) | | | | |
| --- | --- | --- | --- | --- | --- |
|  | 0 | 250 | 500 | 1000 | 2000 |
| Experiment 1 | 3.00 | 3.00 | 2.50 | 0 | 0 |
| Experiment 2 | 3.00 | 3.00 | 2.00 | 0 | 0 |

What is claimed is:

1. A compound having the structure

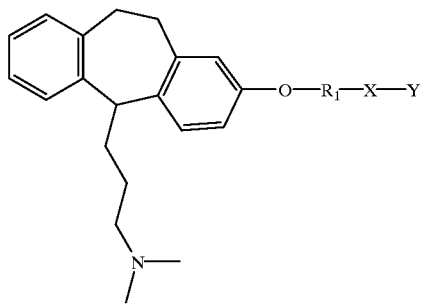

where R1 is a saturated or unsaturated, substituted or unsubstituted, straight or branched chain of 0–10 carbon or heteroatoms, X is a linker group consisting of 0–2 substituted or unsubstituted aromatic rings, and Y is an activated ester or NH—Z, where Z is a poly(amino acid) or polysaccharide.

2. An immunogen having the structure

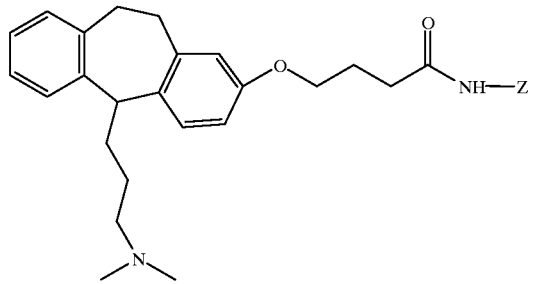

where Z is a poly(amino acid).

3. An antibody produced in response to the immunogen of claim 2.

4. A compound having the structure

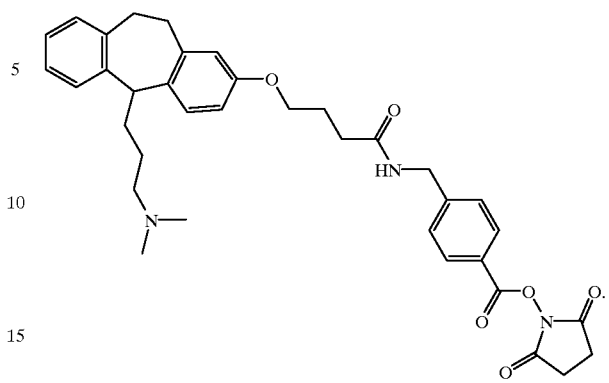

5. A compound having the structure

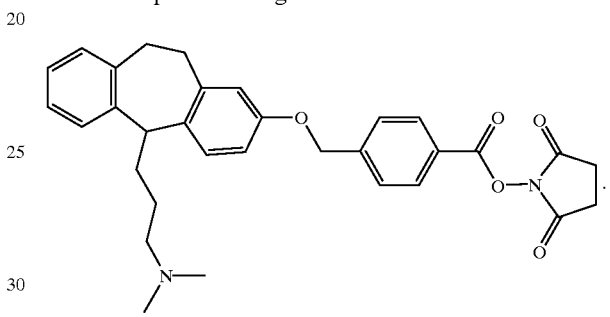

6. A compound having the structure

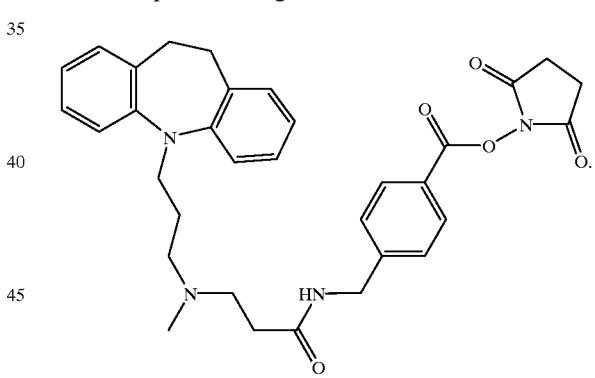

7. A compound having the structure

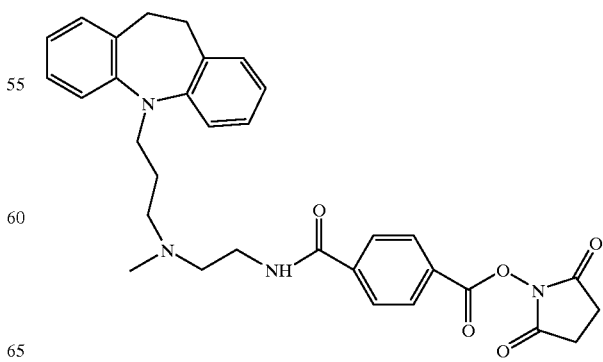

8. An immunoassay method for determining an analyte selected from the group consisting of tricyclic antidepressant drugs, derivatives and metabolites thereof comprising the steps of:

(a) combining a sample suspected of containing said analyte with an antibody specific for said analyte and an analyte analog derived from a compound having a structure selected from the group consisting of

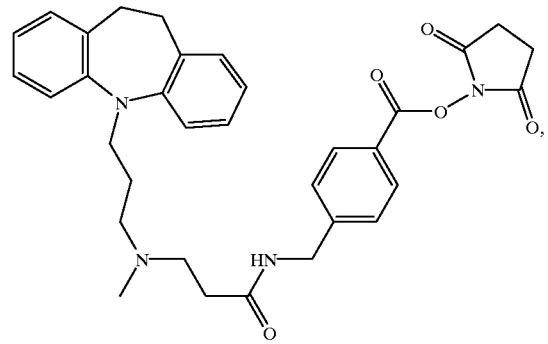

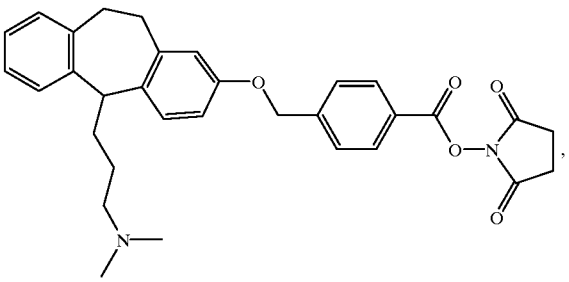

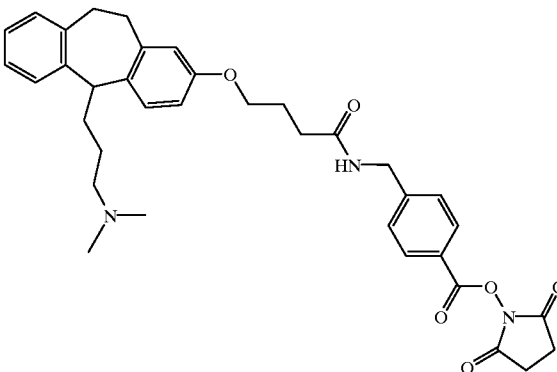

and

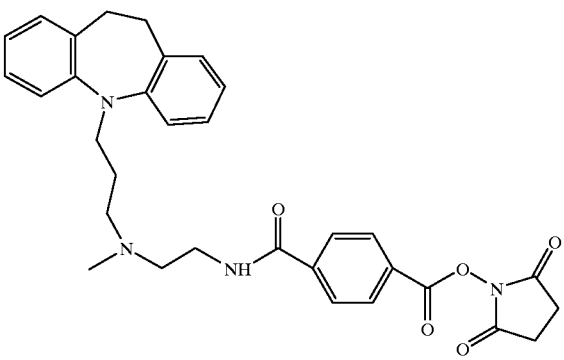

said analog or said antibody comprising a detectable label, under conditions favorable for said analyte and analyte analog to combine with said antibody to form a detectable complex, and (b) determining the presence or amount of said detectable complex as a measure of said analyte in said sample.

9. An immunoassay method for determining an analyte selected from the group consisting of tricyclic antidepressant drugs, derivatives and metabolites thereof comprising the steps of:

(a) combining a sample suspected of containing said analyte with an antibody produced from the immunogen of claim 2 and an analyte analog, said analog or said antibody comprising a detectable label, under conditions favorable for said analyte and analyte analog to combine with said antibody to form a detectable complex, and (b) determining the presence or amount of said detectable complex as a measure of said analyte in said sample.

10. An immunoassay method for determining an analyte selected from the group consisting of tricyclic antidepressant drugs, derivatives and metabolites thereof comprising the steps of:

(a) combining a sample suspected of containing said analyte with an antibody produced from the immunogen of claim 2 and an analyte analog derived from a compound having a structure selected from the group consisting of

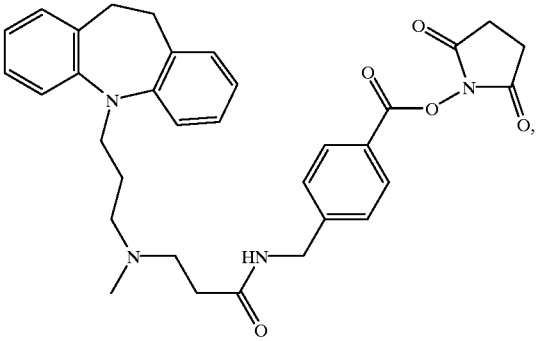

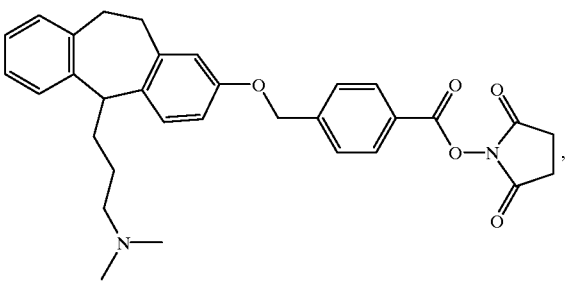

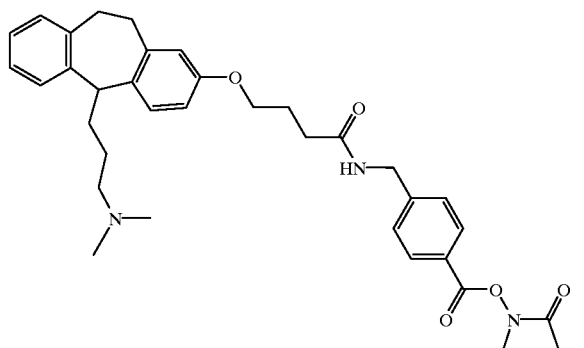
and
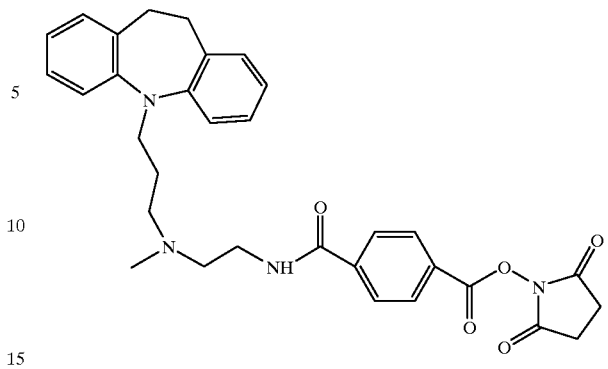
said analog or said antibody comprising a detectable label, under conditions favorable for said analyte and analyte analog to combine with said antibody to form a detectable complex, and
(b) determining the presence or amount of said detectable complex as a measure of said analyte in said sample.
* * * * *